United States Patent

Lyst, Jr. et al.

[11] Patent Number: 6,120,145
[45] Date of Patent: Sep. 19, 2000

[54] SURGICAL LOUPES APPARATUS

[75] Inventors: James E. Lyst, Jr., Carmel; Jeffery J. Segal, Terre Haute, both of Ind.

[73] Assignee: LD3, Inc., Carmel, Ind.

[21] Appl. No.: 09/340,890

[22] Filed: Jun. 28, 1999

[51] Int. Cl.[7] .............................. G02C 1/00; G02B 25/00
[52] U.S. Cl. ..................... 351/158; 359/481; 359/482
[58] Field of Search ................... 351/159; 359/480–482

[56] References Cited

U.S. PATENT DOCUMENTS

| | | | |
|---|---|---|---|
| 2,123,682 | 7/1938 | Wingate | 351/158 |
| 2,594,698 | 4/1952 | Thomas | 359/480 |
| 4,077,703 | 3/1978 | Pablo | 359/480 |
| 4,195,918 | 4/1980 | Freche et al. | 351/158 |
| 4,196,966 | 4/1980 | Malis | 359/482 |
| 4,364,645 | 12/1982 | Feinbloom | 351/204 |
| 4,457,584 | 7/1984 | Pryor | 359/477 |
| 4,540,238 | 9/1985 | Edwards | 359/481 |
| 4,674,845 | 6/1987 | Matsumura | 359/381 |
| 4,704,000 | 11/1987 | Pekar et al. | 359/482 |
| 4,710,000 | 12/1987 | Spitznas et al. | 359/377 |
| 4,795,235 | 1/1989 | Spitzberg | 359/404 |
| 4,863,468 | 9/1989 | Feinbloom et al. | 623/6 |
| 4,877,316 | 10/1989 | Edwards et al. | 359/409 |
| 5,028,127 | 7/1991 | Spitzberg | 351/158 |
| 5,076,682 | 12/1991 | Pasfield | 351/158 |
| 5,078,469 | 1/1992 | Clark et al. | 359/481 |
| 5,223,863 | 6/1993 | Heine et al. | 351/205 |
| 5,579,158 | 11/1996 | Pandula | 359/482 |
| 5,680,194 | 10/1997 | Pasfield | 351/158 |
| 5,680,195 | 10/1997 | Pekar et al. | 351/158 |
| 5,680,250 | 10/1997 | White | 359/479 |
| 5,870,166 | 2/1999 | Chang et al. | 351/158 |
| 5,920,371 | 7/1999 | Chang et al. | 351/158 |
| 5,923,467 | 7/1999 | Pericic et al. | 359/411 |

FOREIGN PATENT DOCUMENTS

WO 96/26415   8/1996   WIPO.

*Primary Examiner*—Huy Mai
*Attorney, Agent, or Firm*—Bose McKinney & Evans LLP

[57] ABSTRACT

An apparatus for changing the direction of light incident on a surgical loupes, the loupes having two optical barrels each optical barrel having an optical assembly with an optical axis. The apparatus includes at least one optical member for redirecting light incident onto said optical assemblies from a desired direction at an angle to the optical axis of said optical assemblies; an attachment member to secure said at least one optical member to the barrels; and an alignment member for calibrating the orientation of the at least one optical member relative to the optical assemblies of the barrels so that the at least one optical member is oriented to redirect the light from said desired direction generally along the optical axes of said optical assemblies of the barrels.

20 Claims, 17 Drawing Sheets

SURGICAL LOUPES APPARATUS

TECHNICAL FIELD OF THE INVENTION

The present invention relates to the field of surgical loupes and in particular to a surgical loupes apparatus that changes the direction light enters the loupes while maintaining the pre-existing optical axis of the loupes barrels, to improve the ergonomics of the surgical loupes.

BACKGROUND OF THE INVENTION

Surgical loupes have been used for decades to more easily allow the surgeon to view small tissue structures or objects. One field of use for surgical loupes is neurosurgery. A surgeon is required to manipulate tiny nerve tissue structures for prolonged periods of time during surgery. A surgical loupes system can magnify the nerve tissues and make it easier for the surgeon to distinguish between different structures. Also, procedures can be accomplished that would be near impossible with the unaided eye.

Surgical loupes, in addition to magnifying the object of interest, also allow the surgeon to view the object of interest at a comfortable distance. For instance, small print in a document can be magnified and hence read by holding the document close to your eyes. However, this produces a great strain on the eyes to focus on an object at such close proximity to the eyes. If the small print could be enlarged and viewed from a distance, the print could be read with minimal strain to the eyes. Surgical loupes accomplish this task, by viewing an object at a comfortable distance and magnifying the size of the object of interest.

Surgical loupes typically have two sets of magnifying optical assemblies housed within barrels, one set for each eye. The optical axes of the two optical assemblies converge to a point in space. This point is the theoretical location of the object to be viewed. It is important to maintain this convergence between the two optical assemblies in order to insure a high quality, stereoscopic image.

Current surgical loupes use either a Galilean or Keplerian telescope optical configuration for the optical assemblies within the barrels. The objective lens or lens system is a positive or converging lens in both the Galilean and Keplerian configurations. The eyepiece or lens system nearest the eye is a positive or converging lens in a Keplerian system and is a negative or diverging lens in a Galilean system. The Keplerian design is well suited for higher magnification, but requires a long barrel and an image inverting/reverting member to produce a high quality image with the correct orientation at the retinal plane of the eye. If the image inverting/reverting member was not included, the image entering the eye would be flipped vertically and left to right. Therefore, if the object of interest was an arrow pointing upward to the right, the image entering the eye would be an arrow pointing downward and to the left. The Galilean designs are shorter and lighter, but are limited in their magnification power. They also have a much larger objective lens than the Keplerian design, which increases the weight of the system.

Surgical loupes differ in how they are worn by the surgeon. The four most common mounting methods are listed in Table 1 along with a manufacturer of an example system.

TABLE 1

Current Surgical Magnifier Categories

| Category | Maker |
| --- | --- |
| Adjustable Head Mounted Systems | Carl Zeiss, Inc. http:\\www.zeiss.com |
| Through-the-Eyeglass Lens Systems | Designs for Vision, Inc. http:\\www.designsforvision.com |
| Adjustable Eyeglass Mounted Systems | Keeler Optics http:\\www.keelerusa.com |
| Combination Systems | LuxTec http:\\www.luxtec.com |

An adjustable head mounted system provides a band which fits around the head of the surgeon and has a set of surgical loupes attached to the band that can be positioned in front of the eyes of the surgeon. The loupes can be rotated up out the line of sight of the surgeon when not in use. Each loupe swivels about a common axis to allow the surgeon to adjust their separation relative to each other. This permits the loupes to be optimized for the pupil separation of the surgeon. The downward tilting of the loupes can also be adjusted. This permits a surgeon to adjust the declination angle of the surgical loupes.

A through-the-eyeglass lens system provides a normal pair of eyeglass frames, to eyeglass lenses with an aperture formed within each lens and a surgical loupe barrel disposed within each lens aperture. This type of system is not adjustable for different pupil separations or different tilting angles of the barrels. The pupil separation of the user must first be measured and then the lens apertures formed to match the measured pupil separation. If the surgeon is required to wear prescription eyewear, his prescription can be built into the magnification optics of the barrels.

An adjustable eyeglass mounted system provides a normal pair of eyeglass frames, eyeglass lenses and a surgical loupes system attached to the bridge of the eyeglass frames that can be positioned in front of the eyes of the surgeon. The loupes can be rotated up out the line of sight of the surgeon. The loupes are laterally adjustable to accommodate various pupil separations. An advantage of this system is that it works well for surgeons that already have to wear prescription eyewear. Because they can view through the loupes or flip the loupes up and view through their normal prescription which can be built into the eyeglass lenses.

The combination systems utilize both the head band and eyeglass frame technologies for mounting their loupes. These systems typically are adjustable and allow for the loupes to be rotated out of the line of sight of the user. In addition, these systems as well as the others might have light sources attached to them to illuminate the object of interest.

The loupes barrels in a surgical loupes system are typically tilted downward at a fixed angle. Although some systems allow the angle of tilt to be adjusted, the tilting of the barrels requires the surgeon to cast his/her eyes downward to see through the loupes. This tilting is required for two reasons. First, the subject matter to be viewed during surgery is typically lying on a table below the line of sight of the surgeon. Second, it is more comfortable, over the duration of surgery, for the surgeon to cast his/her eyes downward than tilting his/her head forward. The angle of tilt of the loupes barrels is referred to as the declination angle.

The declination angle of the loupes is defined as the angle between the support line of the loupes and the actual line of sight of the user through the loupes. The support line is generally parallel to the straight ahead line of sight of the surgeon. Therefore, the declination angle is a measurement of the angle by which the eyes of the surgeon are cast downward relative to looking straight ahead. In the case of eyeglass mounted systems, the support line is an imaginary line connecting the superior auricular crevice of the ear, the location at which the eyeglass frames rest on the ear, to the point on the nose where the eyeglass frames rest. Research has shown the ideal declination angle is different for all surgeons, but is in the range from 15° to 44° with a mean of 34°. This means an average surgeon can cast their eyes downward 34° for extended periods of time. However, this downward casting is not as comfortable as looking straight ahead or downward at a slight angle. A majority of through-the-eyeglass lens systems can achieve declination angles between 10° and 22°. Although some systems can achieve up to 45°. A significant percentage of adjustable loupes are not able to achieve a declination angle greater than 34°.

When the declination angle of the surgical loupes does not match the ideal declination angle for a particular surgeon, or the desired subject matter is not in the field of view of the loupes, the surgeon compensates in two different ways. First, the surgeon will increase the downward casting of his/her eyes. Over prolonged periods of time, such as surgery, this will cause a straining of the intrinsic and extrinsic eye musculature. Second, the surgeon will tip his/her head forward and downward in order to see the subject matter through the loupes. Over prolonged periods of time, such as surgery, this will cause a straining of the head, neck and shoulder musculature. These additional strains on the musculature of the body increase fatigue and lead to potential risk of extended or permanent disabilities.

Current surgical loupes, although state of the art, have four main drawbacks. First, they require the surgeon to cast his/her eyes downward. This downward casting, although less physically demanding than head tilting, places undue strain on the body of the surgeon. Ideally the surgeon should be able to look straight ahead or downward at a slight angle. Second, the loupes do not always allow the surgeon to view the subject area they desire to view. The surgeon must compensate by leaning forward and/or tilting his/her head. Third, loupes that do not have an adjustable tilting or declination angle are not always matched to the ideal declination angle of the surgeon. Therefore, the surgeon must cast his/her eyes at an angle that does not match their ideal declination angle. This places added stress on the eyes of surgeons. Fourth, the location of the barrels limits the surgeon from seeing the object of interest non-magnified. This could limit the surgeon's ability to correlate the magnified image through the loupes with the overall surroundings of the object of interest.

SUMMARY OF THE INVENTION

The present invention is an apparatus for changing the direction of light incident on a surgical loupes, the loupes having two optical barrels moveable relative to each other and each optical barrel having an optical assembly with an optical axis. The present invention includes a housing, at least one optical member for redirecting light incident onto the optical assemblies of the loupes from a desired direction which is at an angle to the optical axes of the optical assemblies of the loupes, a member for coupling the at least one optical member to the housing, an attachment member to secure the housing to the loupes barrels so that the at least one optical member is oriented to redirect light from the desired direction generally along the optical axes of the loupes optical assemblies, and an alignment member to maintain the orientation of the at least one optical member relative to the optical assemblies of the loupes barrels when the barrels are moved. The alignment member can also be used to calibrate the orientation of the at least one optical member relative to the optical assemblies of the loupes. The present invention can also be used with surgical loupes systems that have fixed barrels.

In one illustrative embodiment of the present invention, two mirrors are adhesively coupled to a generally hollow housing. The housing has the alignment member disposed at a first end. The alignment member includes a partially exposed cylindrical cavity. An attachment member is secured to each loupes barrel and each member has an outward-facing, spherical surface. The spherical surface of each attachment member is disposed and captively held by the cylindrical cavity of the alignment member. The attachment members are free to move along the axis of the cylindrical cavity, but not radially.

When the distance between the loupes barrels is adjusted, the attachment members move with the barrels. If the barrels move both upward and outward or downward and inward, the alignment member moves upward or downward. This is because the attachment members can only move inward or outward relative to the alignment member. The movement of the alignment member moves the housing which in turn moves the two mirrors. Therefore, the alignment member keeps the two mirrors positioned in front of the loupes barrels and in the correct orientation.

In a second illustrative embodiment, the two mirrors in the first illustrative embodiment are replaced with two prisms. The mirrors in the first embodiment spanned both loupes barrels and redirected light from the desired direction along the optical axes of the loupes optical assemblies. The prisms in this embodiment are positioned one in front of each loupes barrel. Each prism redirects light from the desired direction along the optical axis of its respective loupes optical assembly. Functionally, the second embodiment is the same as the first embodiment.

A third illustrative embodiment has a two piece housing member each with a prism secured thereto. Each housing member has an outward-facing, spherical surface. The embodiment also has a two piece attachment member. Each attachment member has an inward-facing, spherical surface. Each housing member is positioned such that its outward-facing, spherical surface is in contact with the inward-facing, spherical surfaces on one of the attachment members. Both attachment members captively hold their respective housing member against the front of one of the surgical loupes barrels. Each attachment member is secured to their respective loupes barrel. Each housing member once assembled is free to rotate about the spherical center of their spherical surface relative to the spherical center of the spherical surface of their respective attachment member.

When the distance between the loupes barrels is adjusted, the attachment members, housing members and prisms move with the barrels. Each housing member has a cylindrical slot in its spherical surface that extends beyond its respective attachment member when assembled. These slots captively hold the alignment member which is a cylindrical rod. This relationship between the alignment member and the housing slots couples the two housing members together so that they rotate by the same amount, but in opposite directions, when the loupes barrels are moved relative to each other.

A fourth illustrative embodiment is almost identical to the third illustrative embodiment. Each attachment member is attached to their respective loupes barrel and each inward-facing, spherical surface faces away from the barrels instead of towards the barrels. Each attachment member also has a set of two hooks. Each housing member is positioned such that its outward-facing spherical surface is in contact with the inward-facing spherical surface of the corresponding attachment member. Each housing member also has a support member protruding outward. The alignment member includes a bar and straps. The bar rests on the housing support members of each housing member. The bar has straps wrapped around it which are connected to the hooks on the attachment members. The straps hold the bar against the housing members and the housing members against the attachment members.

As in the third embodiment, the housing members are free to rotate relative to their respective attachment members. Once again, the alignment member couples the two housing members together so that they rotate by the same amount, but in opposite directions, when the loupes barrels are moved relative to each other.

It is an object of the present invention to provide a surgical loupes apparatus that can be attached to any existing surgical loupes and used to correct for any discrepancy between the loupes declination angle and the ideal declination angle of the surgeon.

It is another object of the present invention to provide a surgical loupes apparatus that will allow for the loupes declination angle to be minimized or zero-valued while still allowing the surgeon to see light from the desired direction. This will greatly improve the ergonomics of using a surgical loupes system during surgery.

It is a further object of the present invention to provide a surgical loupes apparatus that maintains its redirection ability when the barrel separation on a pair of surgical loupes is adjusted. This means light still enters the loupes optical assemblies from the desired direction, and the optical axes of the two loupes optical assemblies still converge to a point in space.

It is a yet another object of the present invention to provide a surgical loupes apparatus that has an adjustable optical member. This feature will allow for the direction light is incident on the apparatus to be adjusted.

It is also an object of the present invention to provide a surgical loupes apparatus that does not impede the line of sight of the surgeon when he/she cast his/her eyes downward, in order to view an unmagnified object.

Additional objects, features and advantages of the invention will become apparent to those skilled in the art upon consideration of the following detailed descriptions of the preferred embodiments exemplifying the best mode of carrying out the invention presently perceived.

DETAILED DESCRIPTION

The present invention is a surgical loupes apparatus which changes the direction light enters a pair of surgical loupes barrels while maintaining the pre-existing optical axis of the loupes optical assemblies within the barrels, to improve the ergonomics of the surgical loupes. Current surgical loupes systems have optical assemblies housed within barrels which are positioned in front of the eyes of the user. The term barrels is used to identify the housings for the loupes optical assemblies and should not be limiting in relation to the shape of the optical assembly housings. Example shapes for the barrels are cylindrical, rectangular, faceted, and tapered. The optical assemblies magnify objects in their line of sight to aid the user in viewing and possibly manipulating the objects. The optical axes of the optical assemblies also converge to a point in space, typically the object of interest. This convergence creates a stereoscopic image of the object of interest.

Surgeons typically work with tissue structures lying on a table located in front of them and below their heads. Surgeons can view the desired tissue structures by either tilting their head forward and/or casting their eyes downward. The majority of surgeons prefer to cast their eyes downward as opposed to tilting their head. However, it would be advantageous if they did not have do either one. The barrels and optical assemblies in surgical loupes are usually tilted downward so that surgeons can view their subject matter by casting their eyes downward instead of tilting their head. The angle subtended between the support line of the loupes and the line of sight through the loupes is known as the declination angle.

Figure 1:
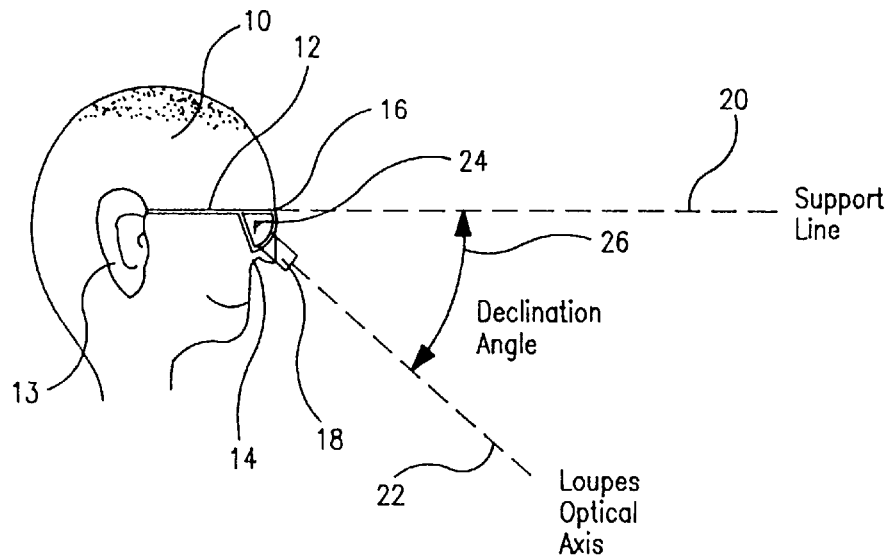
FIG. 1 is a pictorial representation of the definition for the surgical loupes declination angle.

Referring to FIG. 1, a pictorial definition of the declination angle for a set of surgical loupes is shown. A user's head 10 is shown with an eyeglass frame 12 resting on the user's ear 13 and nose 14. Eyeglass frame 12 includes eyeglass lenses 16 secured to frame 12. Eyeglass lenses 16 have surgical loupes barrel optical assemblies 18 secured therein. The imaginary line connecting eyeglass frame 12 rest points on ear 13 and rest points on nose 14 is shown as support line 20. The optical axis of surgical loupes barrel optical assemblies 18 is shown as loupes optical axis 22. The eyes 24 of the user are cast downward to view along loupes optical axis 22. The angle subtended between support line 20 and loupes optical axis 22 is defined as the declination angle 26 of the system.

Figure 2:
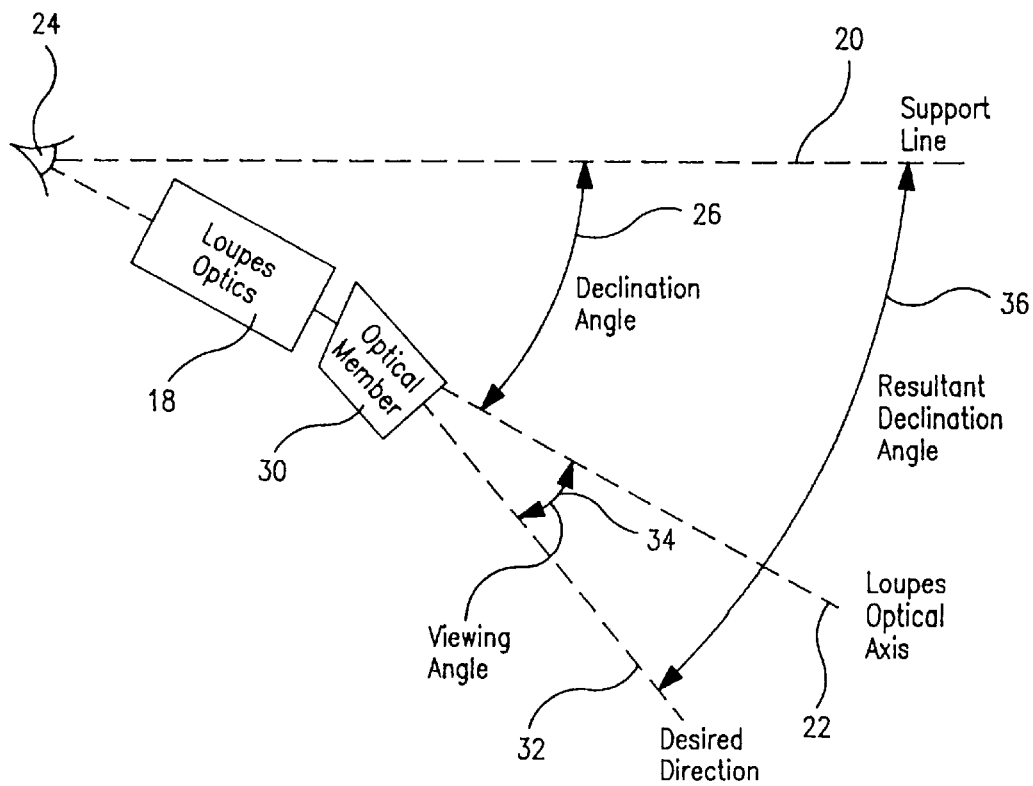
FIG. 2 is a pictorial representation of the definition of the viewing angle of the present invention and the resultant declination angle.

FIG. 2 shows a pictorial representation of the definition of the viewing angle and resultant declination angle of the present invention. Referring to FIG. 2, the present invention incorporates an optical member 30 to change the angle at which light enters surgical loupes optical assemblies 18 and user eye 24. Surgical loupes support line 20 is shown as a reference line. The loupes optical axis 22 is shown extending through the optical member 30 for reference only. Light can only enter optical member 30 generally along the desired direction 32. The angle subtended between loupes optical axis 22 and desired direction 32 is defined as the viewing angle 34 of the present invention. The angle subtended between support line 20 and desired direction 32 is defined as the resultant declination angle 36. Resultant declination angle 36 is the simple addition of declination angle 26 and viewing angle 34.

It will be understood by those of ordinary skill in the art that optical member 30 can be configured so that declination angle 26 equals zero. Therefore, viewing angle 34 is equal to resultant declination angle 36. In this scenario, the user can look straight ahead and still see objects from desired direction 32. This dramatically reduces the amount of strain placed on the eyes and/or body of the user. Declination angle 26 could also be set to any value that is most comfortable to the user. Viewing angle 34 can then be adjusted to ensure that light from desired direction 32 still enters loupes optical assemblies 18. Those of ordinary skill in the art will also understand that viewing angle 34 can act as a supplement to declination angle 26. This scenario allows for a user whose ideal declination angle does not match the declination angle of the surgical loupes to achieve an ideal resultant declination angle 36. It will also be apparent to those of ordinary skill in the art that optical member 30 can be adjustable. Thereby, permitting desired direction 32 to be changed without requiring the user to tilt his/her head or strain his/her eyes.

FIGS. 3–7 show different optical configurations which may be used in the present invention. It should be noted that various combinations of these elements or different optical elements may be used without departing from the spirit and scope of the claimed invention. The only requirement of optical member 30 is to redirect light from desired direction 32 into loupes optical assemblies 18 in the correct orientation and generally along loupes optical axis 22.

Figure 3:
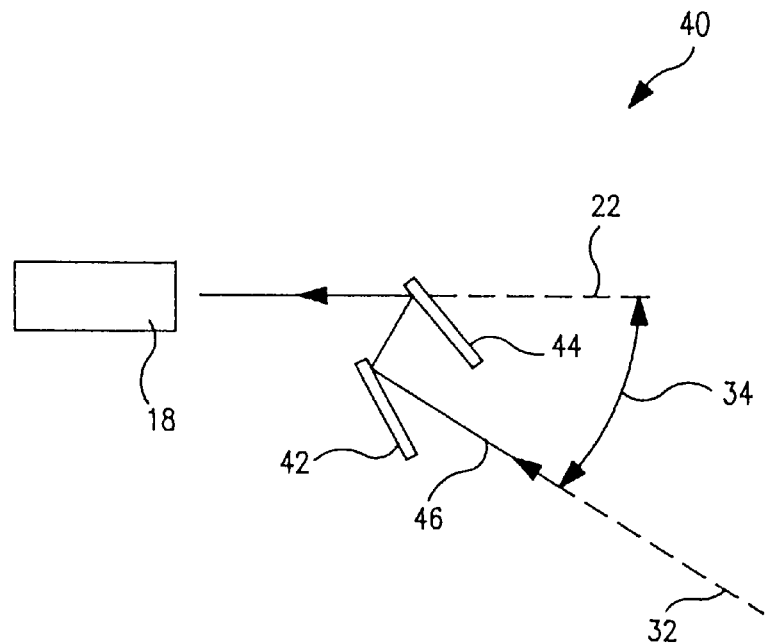
FIG. 3 is a pictorial representation of the optical path through a system of two mirrors.

FIG. 3 shows a two mirror system 40. Light from desired direction 32 reflects off of mirror 42. The reflected light then propagates to and reflects off of mirror 44. The light reflected off of mirror 44 enters loupes optical assemblies 18 along loupes optical axis 22. A ray 46 is used to indicate the path of light through two mirror system 40. Viewing angle 34 in FIG. 3 is 30°. Therefore, two mirror system 40 produces a resultant declination angle 36 equal to loupes declination angle 26 plus 30°. The tilt angles of mirrors 42, 44 can be adjusted to produce a different viewing angle 34. Mirrors 42, 44 should be front surface mirrors with minimal loss such as 3% in the visible spectrum. A front surface mirror has a reflective coating on its front surface opposed to its back surface.

Figure 4:
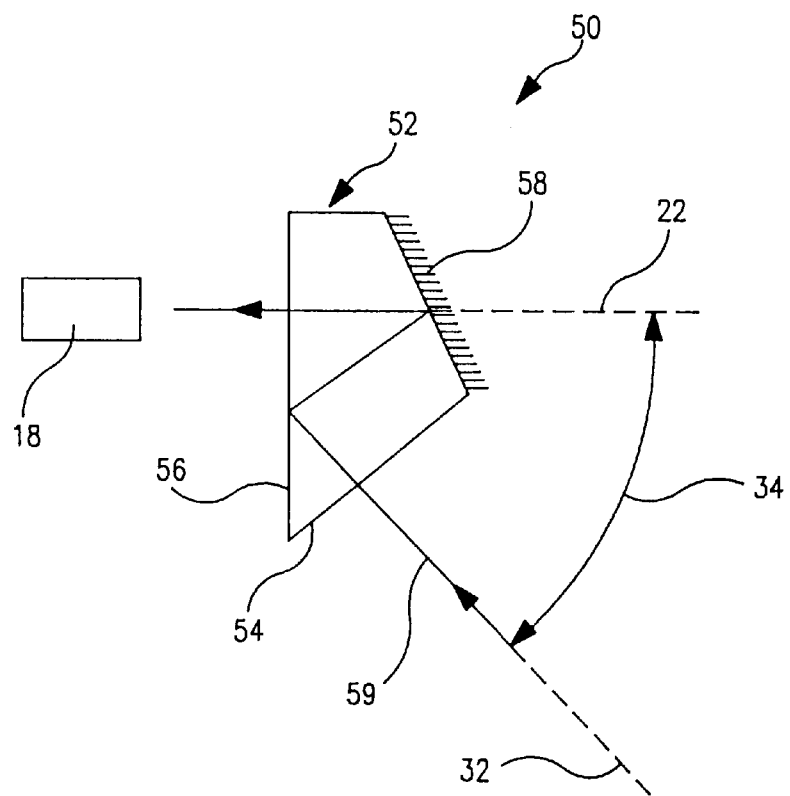
FIG. 4 is a pictorial representation of the optical path through a Bauernfiend prism.

FIG. 4 shows a Bauernfiend prism system 50. Light from desired direction 32 enters prism 52 at surface 54. The light then propagates within the prism to surface 56 where it is reflected due to total internal reflection. The light is reflected at surface 56 because it is incident at an angle smaller than the critical angle for the air-glass interface. This is the same principle that allows light to propagate along the length of an optical fiber. The light reflected at surface 56 then propagates to and reflects off of surface 58, which has a reflective coating applied. The light reflected off of surface 58 exits prism 52 through surface 56 and enters loupes optical assemblies 18 along loupes optical axis 22. A ray 59 is used to indicate the path of light through Bauernfiend prism system 50. Viewing angle 34 in FIG. 4 is 45°. Therefore, Bauernfiend prism system 50 produces a resultant declination angle 36 equal to loupes declination angle 26 plus 45°. The viewing angle can be adjusted by changing the angular relationship between the surfaces of Bauernfiend prism 52.

Figure 5:
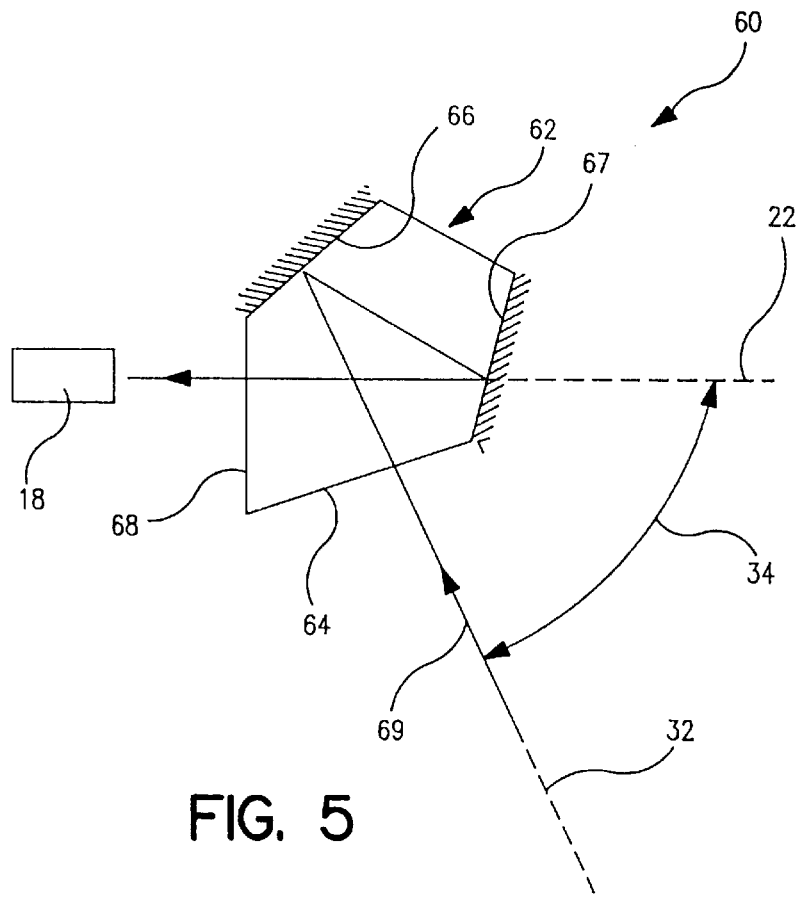
FIG. 5 is a pictorial representation of the optical path through a Penta prism.

FIG. 5 shows a Penta prism system 60. The angular relationship between the surfaces of prism 62 have been modified from a typical Penta prism. Light from desired direction 32 enters prism 62 at surface 64. The light then propagates within prism 62 to surface 66 where it is reflected due to a reflective coating applied to surface 66. The light reflected at surface 66 propagates to and reflects off of surface 67, which has a reflective coating applied. The light reflected off of surface 67 exits prism 62 through surface 68 and enters loupes optical assemblies 18 along loupes optical axis 22. A ray 69 is used to indicate the path of light through Penta prism system 60. Viewing angle 34 in FIG. 4 is 60°. Therefore, Penta prism system 60 produces a resultant declination angle 36 equal to loupes declination angle 26 plus 60°.

Figure 6:
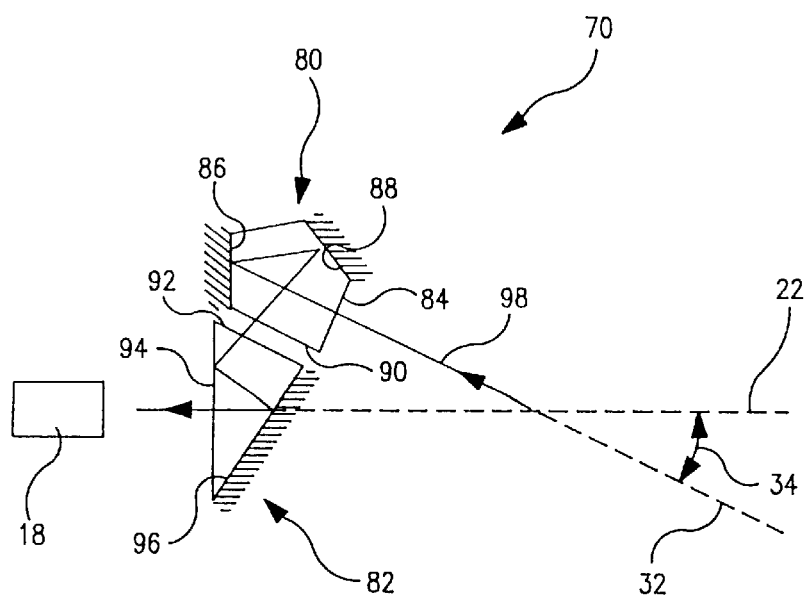
FIG. 6 is a pictorial representation of the optical path through the combination of a Littrow prism and a Penta prism.

FIG. 6 shows a combination system 70. Combination system 70 is comprised of a Penta prism 80 and a Littrow prism 82. Light from desired direction 32 enters Penta prism 80 through surface 84. The light then propagates to and reflects off of surface 86. The reflected light then propagates to and reflects off of surface 88 and exits Penta prism 80 at surface 90. The light from Penta prism 80 enters Littrow prism 82 at surface 92. The light is reflected, due to total internal reflection, at surface 94. The reflected light propagates to and is reflected off of surface 96, exits Littrow prism 82 at surface 94 and enters loupes optical assemblies 18 along loupes optical axis 22. A ray 98 is used to indicate the path of light through combination system 70. Viewing angle 34 in FIG. 6 is 30°. Therefore, combination system 70 produces a resultant declination angle 36 equal to loupes declination angle 26 plus 30°.

Figure 7:
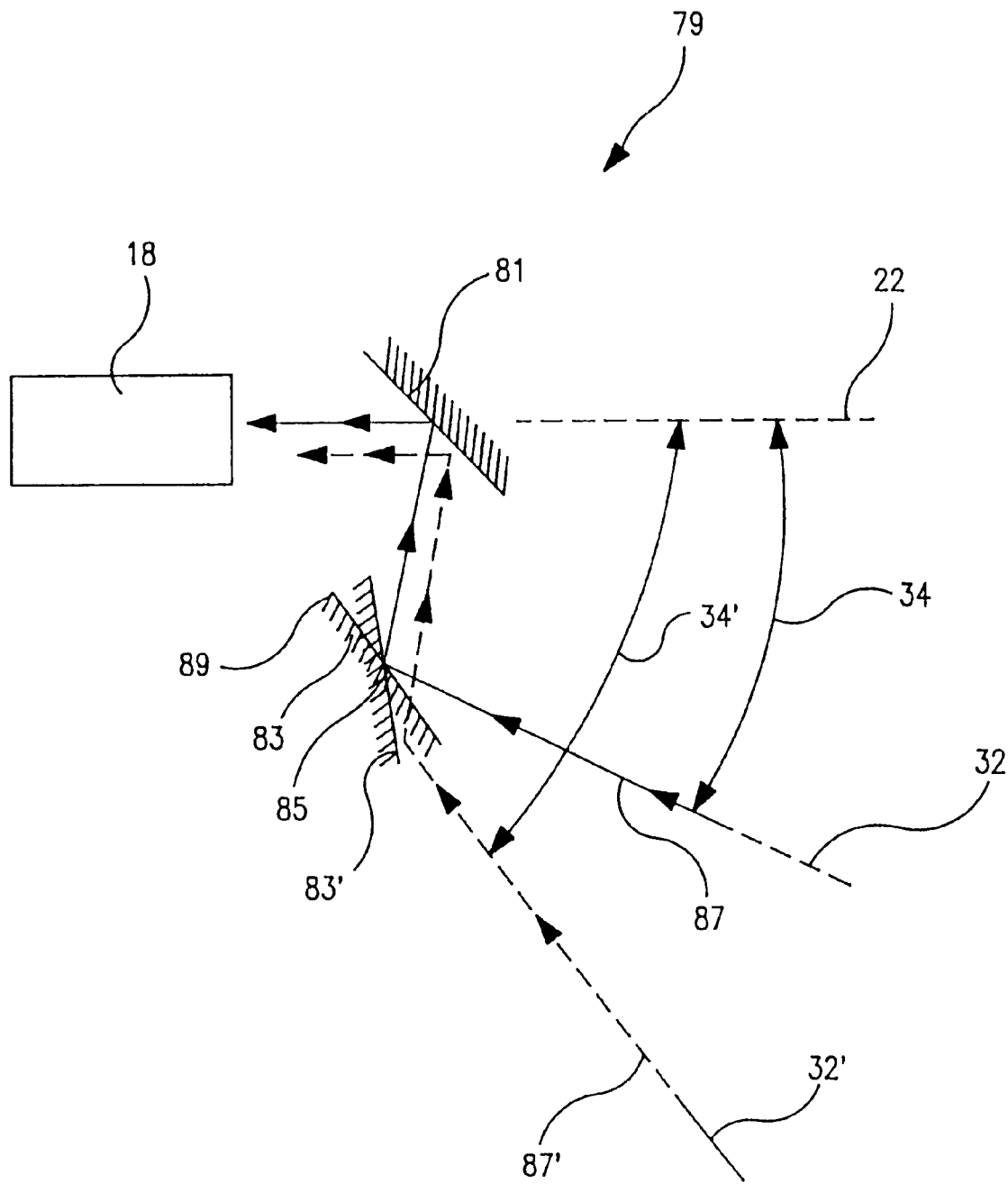
FIG. 7 is a pictorial representation of the optical path through a system of two mirrors, one of which is adjustable.

FIG. 7 shows an adjustable mirror system 79, having at least one mirror adjustable. Light from desired direction 32 reflects off of mirror 83. The reflected light then propagates to and reflects off of mirror 81. The light reflected off of mirror 81 enters loupes optical assemblies 18 along loupes optical axis 22. A ray 87 is used to indicate the path of light through adjustable mirror system 79. Viewing angle 34 is 25° in FIG. 7. Therefore, two adjustable mirror system 79 produces a resultant declination angle equal to the loupes declination angle plus 25°.

Mirror 83 is adjustable. This allows for an adjustable viewing angle 34'. Looking at FIG. 7, mirror 83 is adjusted to its new position 83'. A ray 87' from desired direction 32' shows the path of light through adjustable mirror system 79 with mirror 83 in its 83' position. Viewing angle 34' is 45°. Mirror 83 can be adjusted by any common adjustable technique. In FIG. 7, mirror 83 rotates about an axis 85. Mirror 83 could also be hinged at one of its ends, such as end 89. It should be noted that mirror 81 could also be an adjustable mirror.

It should be noted that in all of the examples provided in FIGS. 3–7, the elements in each optical member 30 do not introduce any optical power into the system. All of the reflective surfaces are generally flat. It is within the scope of the present invention to add either positive or negative optical power to optical member 30 through the addition of lenses, non-flat reflective surfaces, or other means. Some of the advantages of adding power to the system are: the overall focal length of optical assemblies 18 can be adjusted, optical aberrations can be corrected, and additional magnification can be added or subtracted.

FIGS. 8–23 show several embodiments of the present invention. Each embodiment comprises a housing, at least one optical member 30 to redirect light from desired direction 32 along the loupes optical axis 22 of the loupes optical assemblies 18, a member for coupling optical member 30 to the housing, an attachment member to secure the housing to the barrels of the loupes and an alignment member to maintain and/or calibrate the orientation of the at least one optical member 30 relative to the optical assemblies 18 of the barrels when the barrels are moved. The present invention is designed to be compatible with all existing surgical loupes systems. As described earlier, surgical loupes are available in four major classifications: adjustable head mounted systems, through-the-eyeglass lens systems, adjustable eyeglass mounted systems and combination systems. The present invention does not limit any adjustability inherent in any of the aforementioned surgical loupes classifications and maintains the convergence alignment of the two loupes barrels.

Each of the embodiments disclosed, is shown with a particular optical member 30. It should be understood that any optical member disclosed in FIGS. 3–7, other reflective or refractive means, or other redirection means, such as fiber optics could be used.

Figure 8:
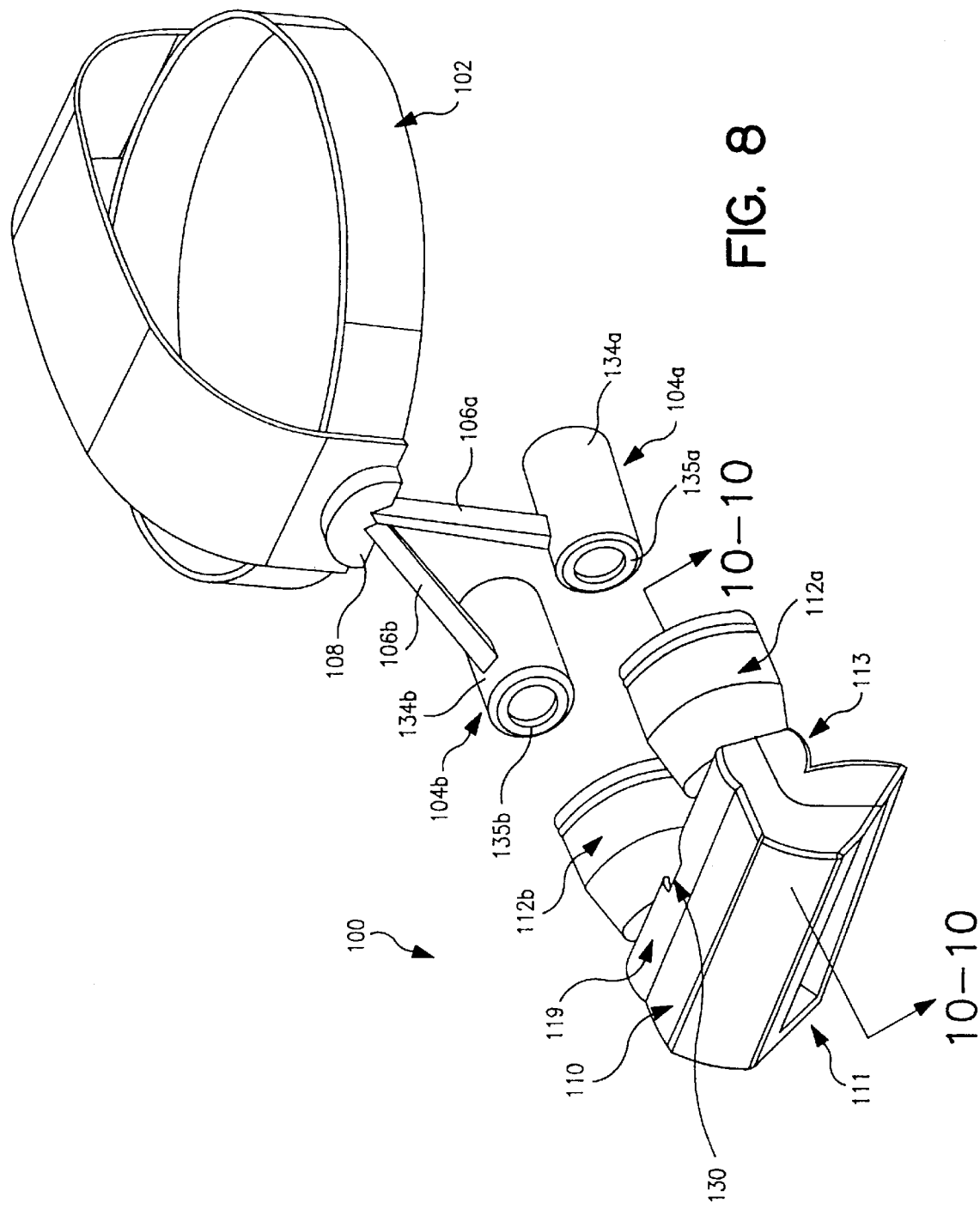
FIG. 8 is a perspective view of a first embodiment of the present invention detached from an adjustable head mounted loupes system.

Referring to FIGS. 8–12, a first embodiment of the present invention, a slide embodiment 100, is shown. Slide embodiment 100 in FIG. 8 is shown in a detached relationship to an adjustable head mounted surgical loupes 102. Adjustable head mounted surgical loupes 102 has two loupes barrels 104a, 104b each containing an optical assembly (not shown in FIG. 8). Each barrel is pivotally mounted to the loupes headband 108 by a barrel arm 106a, 106b. Barrels 104a, 104b pivot about a common axis and are moved or pivoted relative to each other to adjust for various user interocular separations. Adjustable head mounted surgical loupes 102 is used for reference only. Slide embodiment 100 can be used with any existing surgical loupes from the aforementioned classes.

Slide embodiment 100 includes a generally hollow housing 110 with a light entrance end 111 and a light exit end 113; attachment members 112a, 112b to secure housing 110 to each loupes barrel 104a, 104b; an optical member comprising two mirrors 114, 116 (shown in FIG. 10); a coupling member 117 to secure mirrors 114, 116 to housing 110 (shown in FIG. 10); and an alignment member 119 for maintaining the orientation of mirrors 114, 116 relative to loupes barrels 104a, 104b.

Slide attachment members 112a, 112b secure housing 110 to each of the loupe barrels 104a, 104b. Slide attachment members 112a, 112b are identical. Loupes barrels 104a, 104b are also identical. For convenience therefore, the structure and function of attachment member 112a and loupes barrel 104a will be described with the understanding that the structure and function of attachment member 112b and loupes barrel 104b is identical. Attachment member 112a has a radial, inward-facing sleeve surface 132a (shown in FIGS. 9 and 10) whose diameter is slightly larger than loupes radial, outward-facing collar surface 134a. Attachment member 112a has a plurality of small ribs 136a extending radially inward from surface 132a (shown in FIGS. 9 and 10). Ribs 136a define an imaginary circle inside attachment member 112a having a diameter generally the same diameter as loupes collar surfaces 134a.

Attachment member 112a is assembled to loupes barrel 104a by press-fitting ribs 136a over loupes collar surface 134a. Ribs 136a should have a taper or lead-in to ease the assembly of attachment member 112a to loupes barrel 104a. Alternative assembly methods are within the scope and spirit of the claimed invention. Any common method to secure two components together could be used. For instance, attachment member 112a could have an aperture through sleeve surface 132a for accepting a set screw. The set screw would press against loupes collar surfaces 134a to secure attachment member 112a to loupes barrel 104a. Another example would be to use an adhesive to bond attachment member 112a to loupes barrels 104a.

Figure 9:
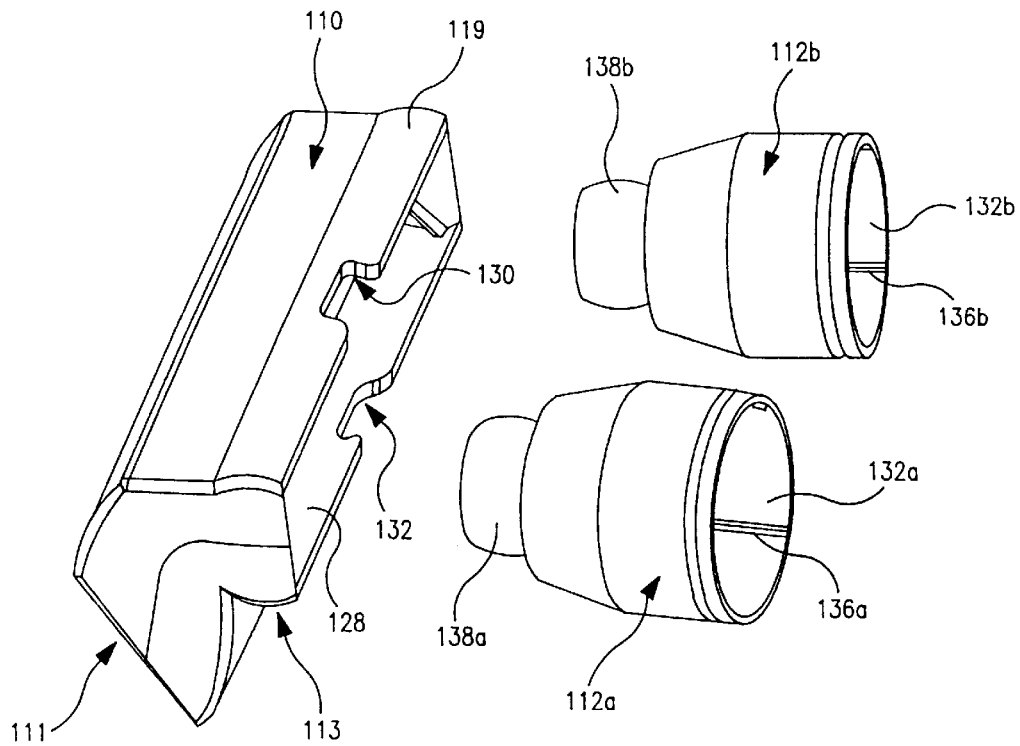
FIG. 9 is an exploded, perspective view of the embodiment shown in FIG. 8.
Figure 10:
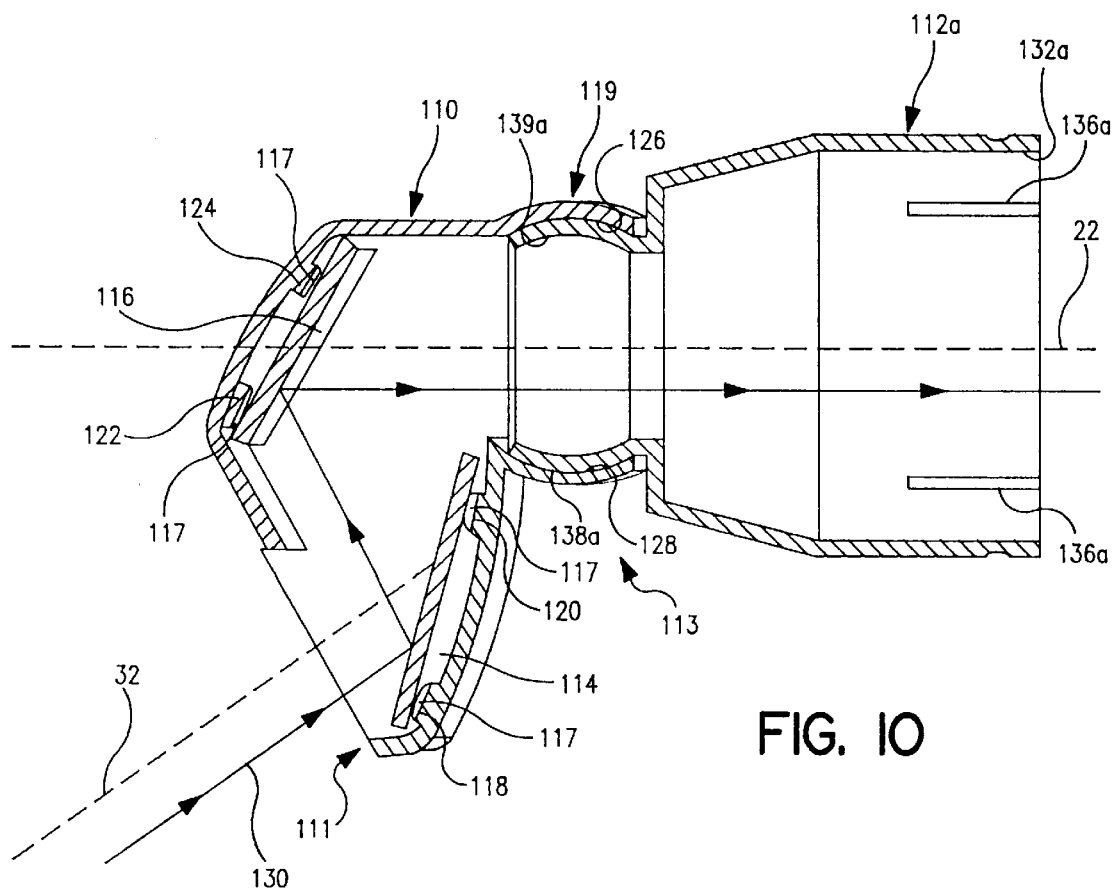
FIG. 10 is a cross sectional view of the embodiment shown in FIG. 8 taken along line 10—10 shown in FIG. 8.
Figure 11:
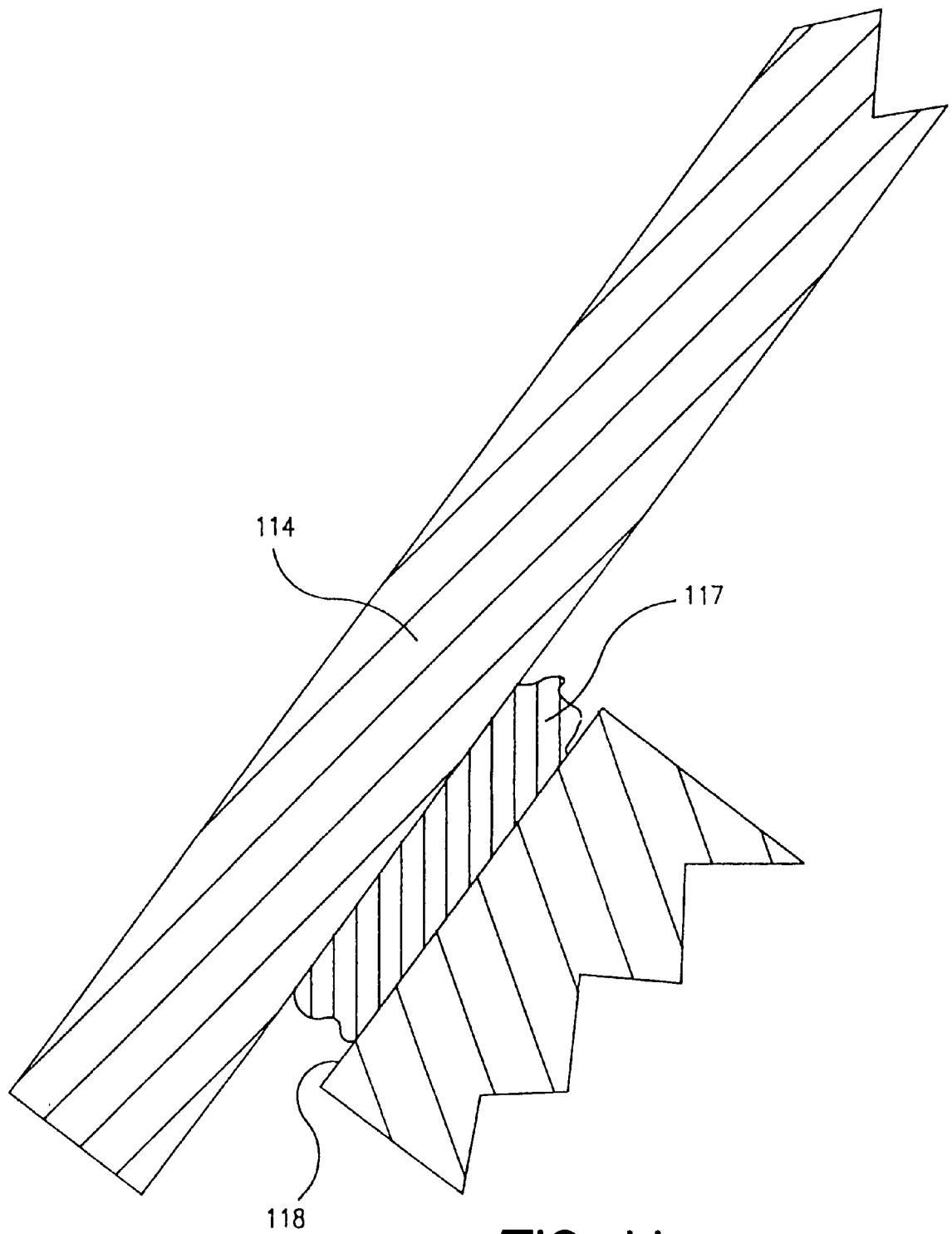
FIG. 11 is a cross sectional view of a portion of the embodiment shown in FIG. 10.

As shown in FIGS. 9 and 10, attachment member 112a has a partial, spherical, radially, outward-facing surface 138a and a partial, spherical, radially, inward-facing surface 139c. Spherical surface 139a and sleeve surface 132a define a cavity which extends completely through attachment member 112a. Attachment spherical surface 138a is used to secure housing 110 to loupes barrel 104a as will be described in the following discussion.

Alignment member 119 is disposed at the exit end 113 of housing 110. Alignment member 119 includes a top, radially, inward-facing cylindrical surface 126 and a bottom, radially, inward-facing cylindrical surface 128. The radius of cylindrical surfaces 126 and 128 are generally identical to the radius of spherical surfaces 138a, 138b of attachment members 112a, 112b. A top relief cut 130 and bottom relief cut 132 are provided in alignment member 119. Relief cuts 130 and 132 are deep enough to intersect the apex or maximum sag of cylindrical surfaces 126 and 128. This allows for the insertsion of surface 138a on attachment member 112a between cylindrical surfaces 126, 128 on alignment member 119.

Referring to FIG. 10, mirrors 114 and 116 are coupled to housing 110 at mounting surfaces 118, 120, 122, and 124 by a coupling member 117. Coupling member 117 is an adhesive, such as epoxy (as shown in detail in FIG. 11). Coupling member 117 could be any standard technique used to mount optical elements to a surface. For example, a felt pad could be used in conjunction with an epoxy. It is also within the scope of the present invention, for coupling member 117 to be a solid member to fix mirrors 114, 116 to housing 110. An example would be a snap feature molded into housing 110 to fixably hold the edges of mirrors 114, 116.

Figure 12:
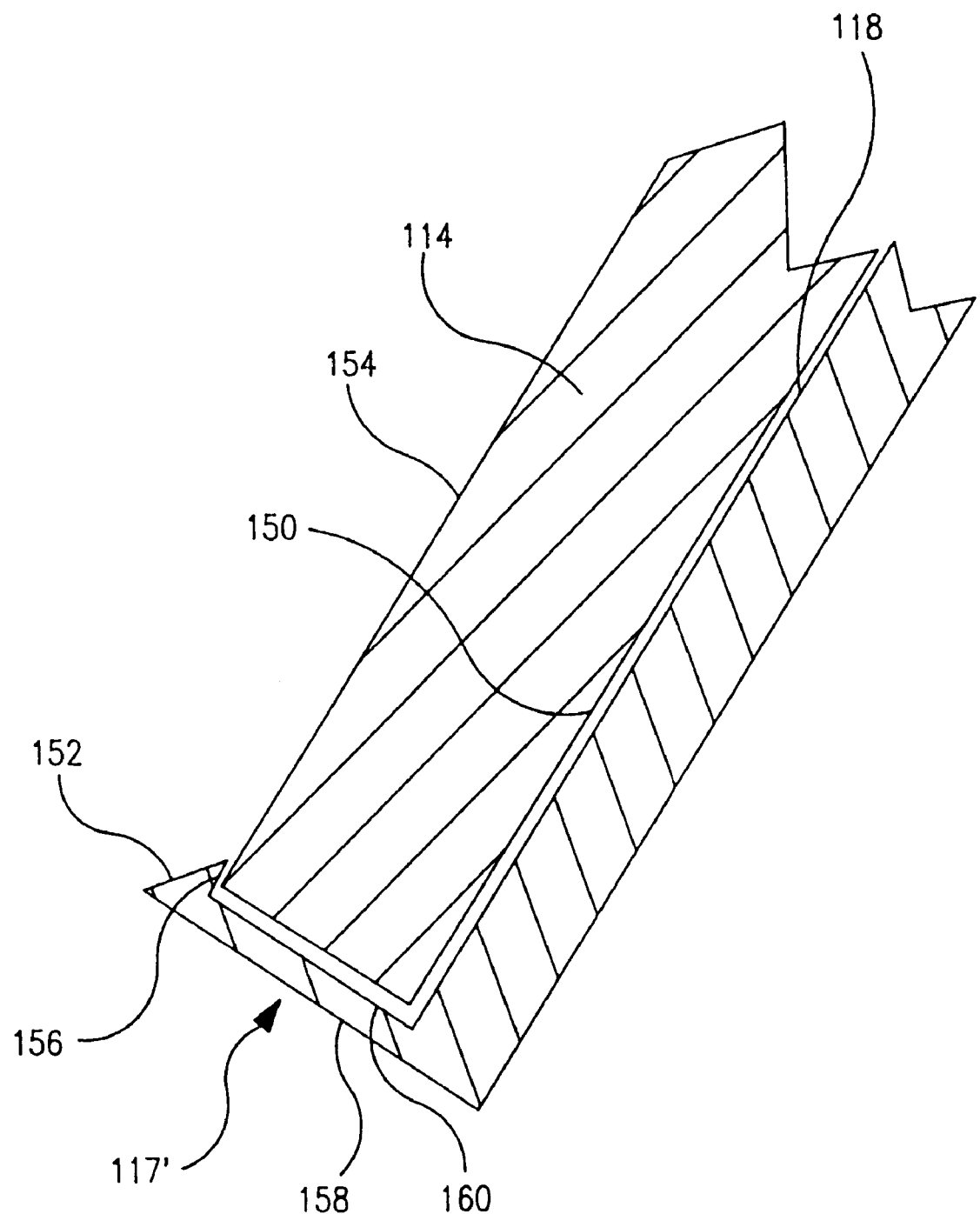
FIG. 12 is a cross sectional view of a snap coupling member of the embodiment shown in FIG. 10.

FIG. 12 shows an example snap coupling member 117'. Coupling member 117' is a protrusion member extending from mounting surface 118. Mirror 114 is assembled in the following manner. Mirror back surface 150 presses against coupling surface 152 thereby causing coupling member 117' and in particular surfaces 158, 160 to flex away from mirror 114. Eventually coupling member 117' flexes enough to allow mirror 114 to slide past surface 152. Once mirror 114 clears surface 152, surfaces 158, 160 snap back to their original positions. Surfaces 156, 160 hold mirror 114 in its correct position.

Slide embodiment 100 is assembled in the following manner. First, mirrors 114, 116 are coupled to housing 110 by coupling member 117. Second, slide attachment members 112a, 112b are secured to loupes barrels 104a, 104b. Third, attachment member 112a is guided through relief cut 130 or relief cut 132 in alignment member 119. Fourth, attachment spherical surface 138a is guided into the cavity formed by alignment cylindrical surfaces 126 and 128 along the axis of cylindrical surfaces 126, 128 and away from relief cuts 130,132 of alignment member 119. Fifth, attachment member 112b is guided through relief cut 130 or relief cut 132 in alignment member 119. Attachment member 112b is guided away from relief cuts 130, 132 of alignment member 119 in the opposite direction relative to attachment member 112a.

The above assembly procedure is only one example of how slide embodiment 100 could be assembled. Additional ordering of the aforementioned steps can be used and are sometimes required to assemble slide embodiment 100. For instance, when loupes barrels 104a, 104b are fixed, i.e. through-the-eyeglass system, slide attachment members 112a, 112b should be secured to loupes barrels 104a, 104b last.

Slide embodiment 100 functions in the following manner. Once slide embodiment 100 has been assembled to adjustable head mounted surgical loupes 102, the user then adjusts the separation of loupes barrels 104a, 104b for their pupil separation. As barrels 104a, 104b are moved outward or inward they also move upward or downward due to their common axis of rotation. Attachment members 112a, 112b move with their respective loupes barrels 104a, 104b and attachment spherical surfaces 138a, 138b slide within alignment member 119 along common the axis of cylindrical surfaces 126, 128.

Alignment member 119 assures that mirrors 114, 116 are always positioned in their correct placement and orientation relative to loupes barrels 104a, 104b. This is accomplished due to the one degree of freedom, along cylindrical axis, alignment member 119 provides attachment members 112a, 112b. As attachment members 112a, 112b move outward and upward, they are only free to move outward within the cavity formed by cylindrical surfaces 126, 128 of alignment member 119. Therefore alignment member 119 must move upward due to the upward movement of attachment members 112a, 112b. The housing 110 moves upward because it is coupled to the alignment member 119. Mirrors 114, 116 also move upward because they are secured to housing 110.

FIG. 10 shows a pictorial view of a ray of light 130 from desired direction 32 moving through slide embodiment 100 and exiting slide embodiment 100 along the loupes optical axis 22. Ray 130 enters the light entrance end 111 of housing 110. Ray 130 is reflected off of mirror 114. The ray is then reflected off of mirror 116 and propagates along loupes optical axis 22.

Figure 13:
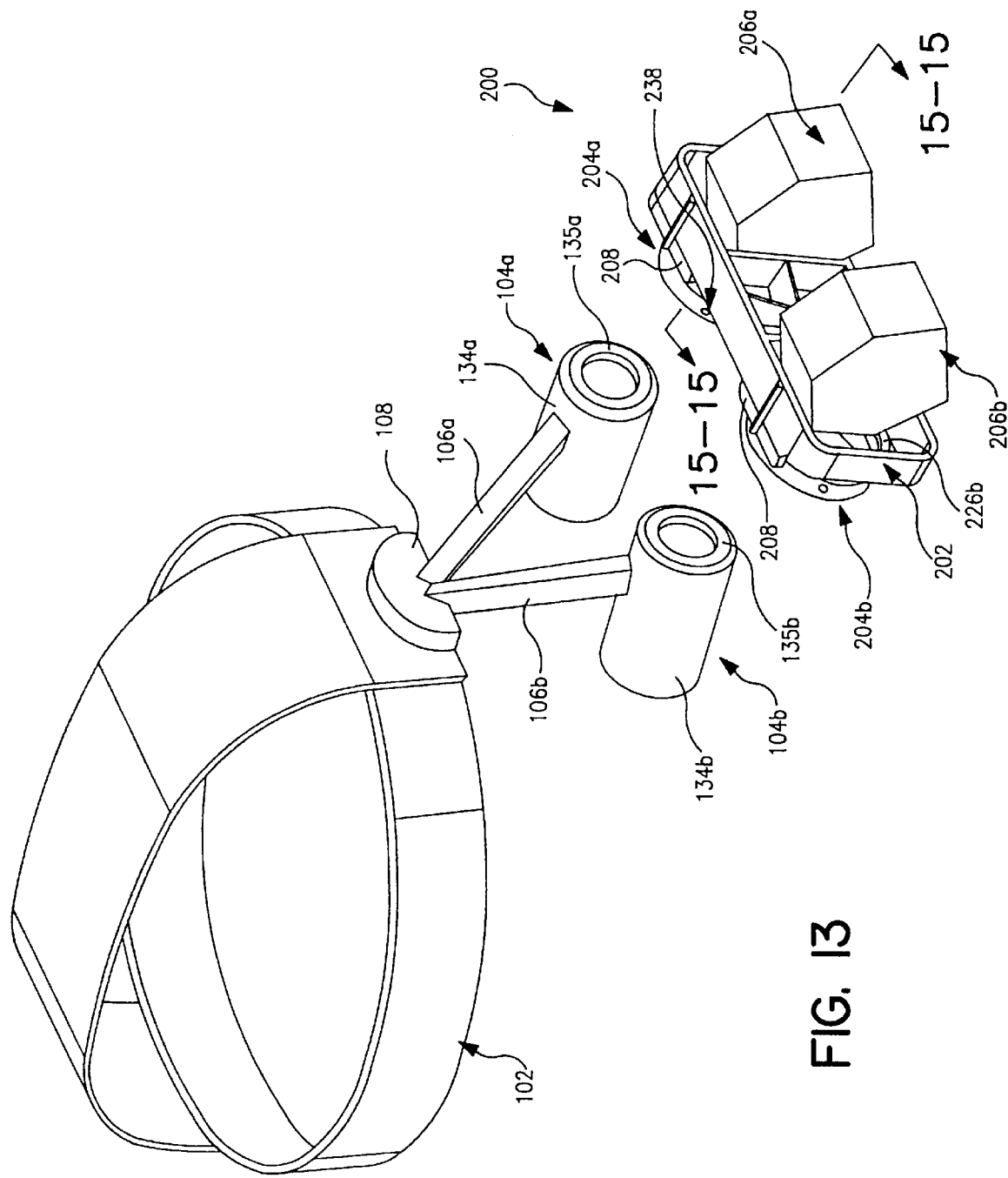
FIG. 13 is a perspective view of a second embodiment of the present invention detached from an adjustable head mounted loupes system.

A second embodiment of the present invention is shown in FIGS. 13–16. This embodiment, hereafter referred to as second slide embodiment 200 is shown in FIG. 13 with an adjustable head mounted loupes 102. Slide embodiment 200 includes a housing 202; a pair of attachment members 204a, 204b to secure housing 202 to each loupes barrel 104a, 104b; a pair of prisms 206a, 206b; an alignment member 208 for maintaining the orientation of prisms 206a, 206b relative to loupes barrels 104a, 104b; and a coupling member 210 (shown in FIG. 15) to secure prisms 206a, 206b to housing 202.

Housing 202 is generally rectangular with two axial cavities formed therethrough. One of the surfaces defining each cavity is a planer surface 212a, 212b. Extending from planer surface 212a, 212b are two optical mounting surfaces, upper optical mounting surface 214a, 214b and lower, optical mounting surface 216a, 216b (shown in FIGS. 14 and 15). Coupling member 210, in this embodiment an epoxy, is applied to upper optical mounting surface 214a, 214b and lower, optical mounting surface 216a, 216b. The prisms 206a, 206b are secured to housing 202 by coupling member 210 (shown in detail in FIG. 16). Other standard optical mounting techniques can be used to couple prisms 206a. 206b to housing 202, such as epoxy and felt pads. Additionally, coupling member 210 could be an integral portion of housing 202, such as a snap feature. Lower optical mounting surfaces 216a, 216b are parallel to each other as are upper optical surfaces 214a, 214b. This parallelism insures that the respective surfaces of prisms 206a, 206b are parallel to each other.

Slide attachment members 204a, 204b secure housing 202 to each of the loupes barrels 104a, 104b. Slide attachment members 204a, 204b are identical. Loupes barrels 104a, 104b are also identical. For convenience, therefore, the structure and function of attachment member 204a and loupes barrel 104a will be described with the understanding that the structure and function of attachment member 204b and loupes barrel 104b are identical.

Figure 14:
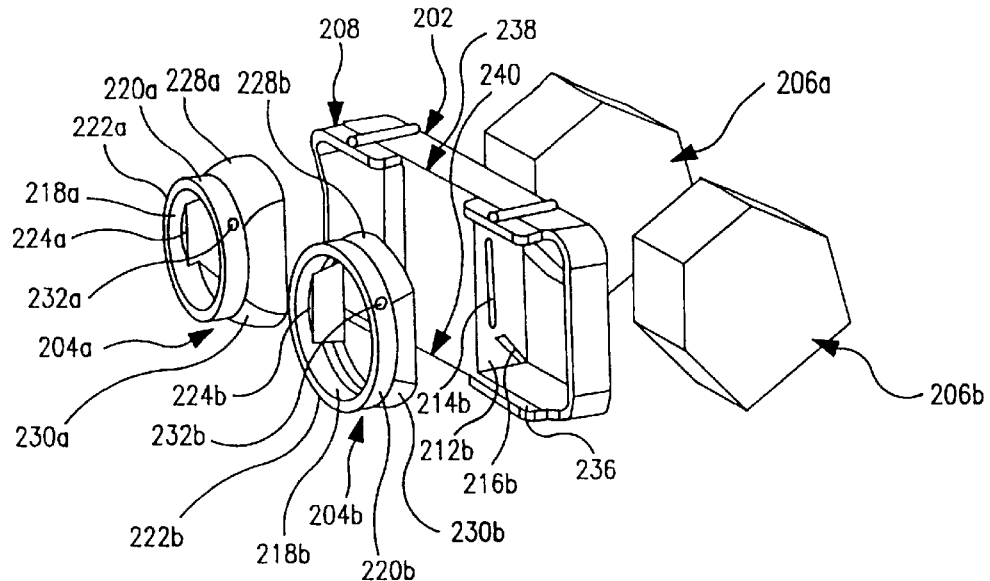
FIG. 14 is an exploded, perspective view of the embodiment shown in FIG. 13.

Referring to FIG. 14, slide attachment member 204a has a radial inward-facing sleeve surface 218a whose diameter is slightly larger than loupes radial outward-facing collar surface 134a, a radial outward-facing surface 220a, an axial outward-facing end surface 222a, an axial, outward-facing stop surface 224a, an axial outward-facing surface 226a and a upper, outward-facing, spherical surface 228a and a lower outward-facing, spherical surface 230a. A set screw aperture 232a extends from radial surface 220a through to radial sleeve surface 218a.

Slide attachment member 204a is secured to loupes barrel 104a in the following manner. First, radial sleeve surface 218a slides over loupes collar surface 134a until axial stop surface 224a is flush against loupes axial surface 135a. Second, a set screw, not shown, is threaded into set screw aperture 232a until it presses against loupes radial surface 134a. The force applied by the set screw holds attachment member 204a onto loupes barrel 104a.

Figure 15:
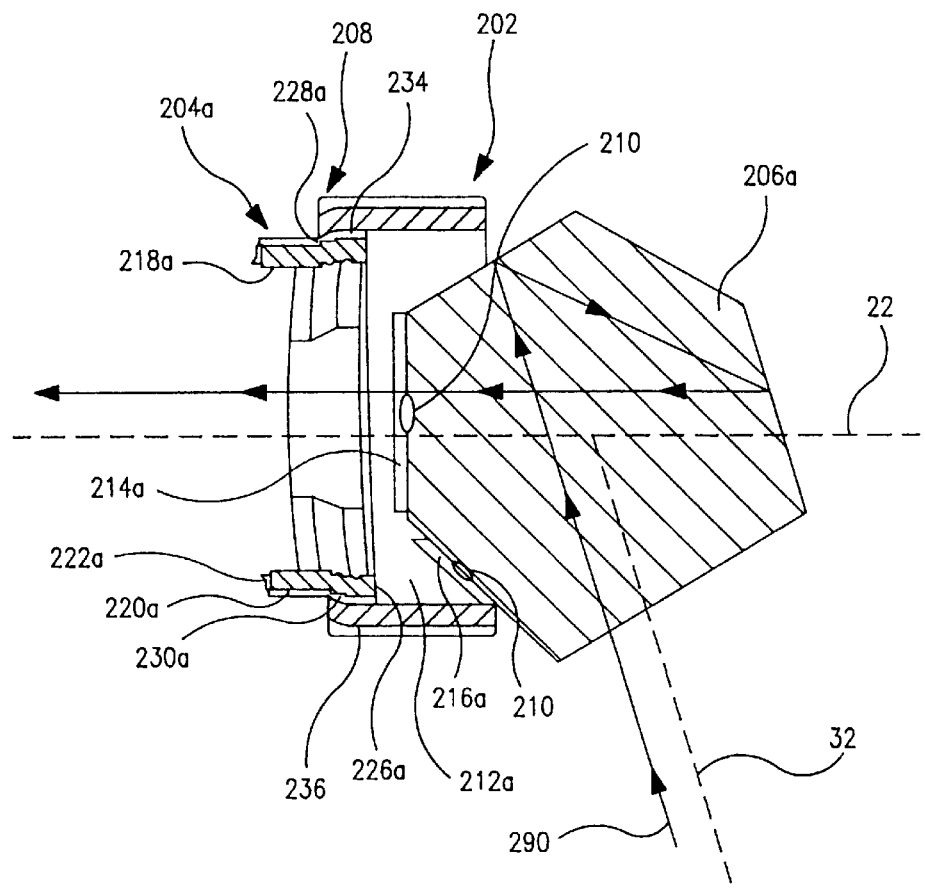
FIG. 15 is a cross sectional view of the embodiment shown in FIG. 13 taken along line 15—15 shown in FIG. 13.
Figure 16:
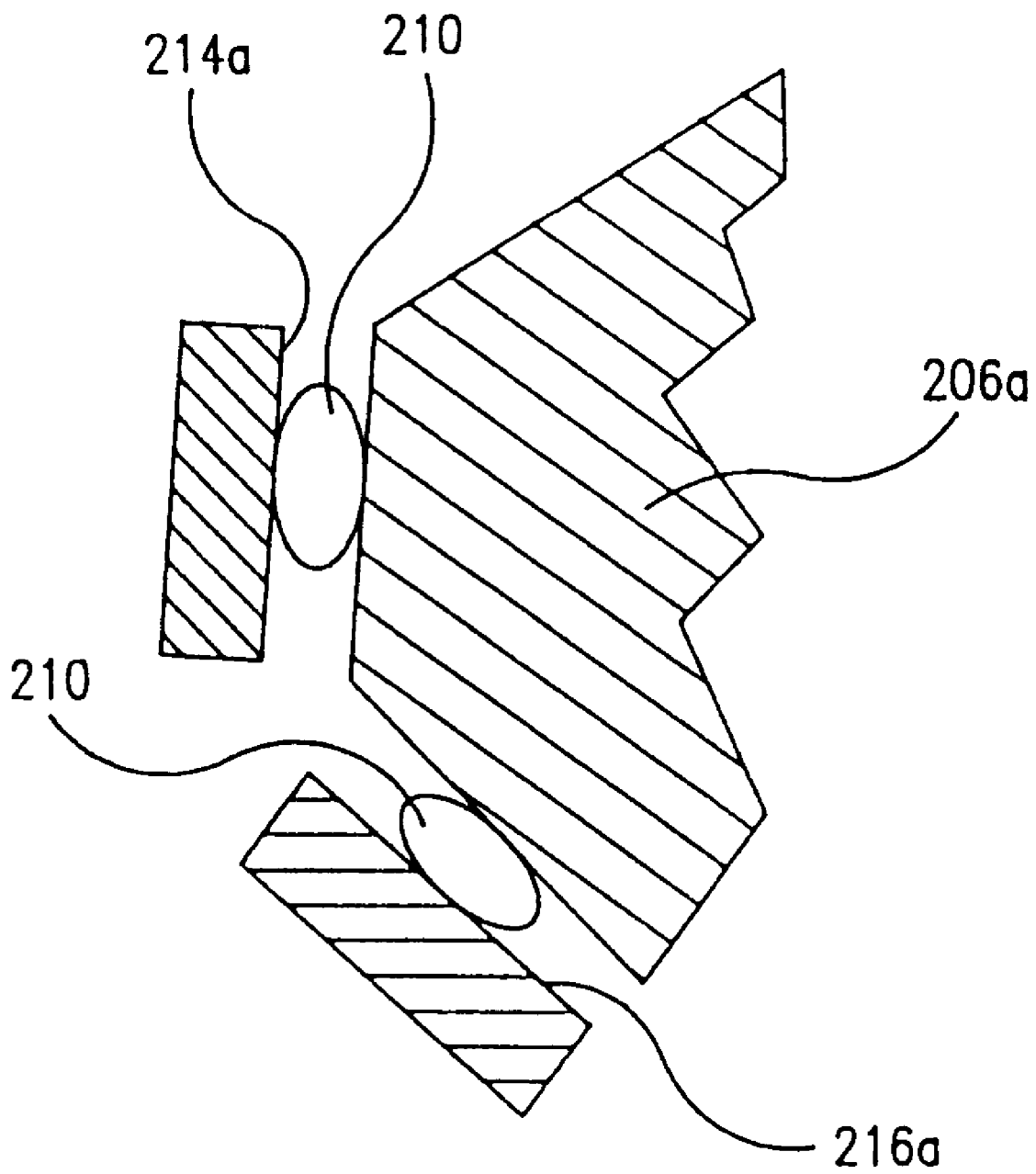
FIG. 16 is a cross sectional view of a portion of the embodiment shown in FIG. 15.

Referring to FIGS. 14 and 15, alignment member 208 includes a top inward-facing cylindrical surface 234 and a bottom inward-facing cylindrical surface 236. The radius of cylindrical surfaces 234 and 236 are generally identical to the radius of spherical surfaces 228a, 230a of attachment member 204a. A top relief cut 238 and bottom relief cut 240 are provided in alignment member 208. Relief cuts 238 and 240 are deep enough to interest the apex or maximum sag of cylindrical surfaces 234 and 236. This allows for the insertion of surfaces 228a, 230a on attachment member 204a between cylindrical surfaces 234, 236 on alignment member 208.

Slide embodiment 200 is assembled and functions in the same manner as slide embodiment 100. It should be noted that if prisms 206a and 206b were one continuous prism slide embodiment 100 would be completely analogous to slide embodiment 100.

Figure 17:
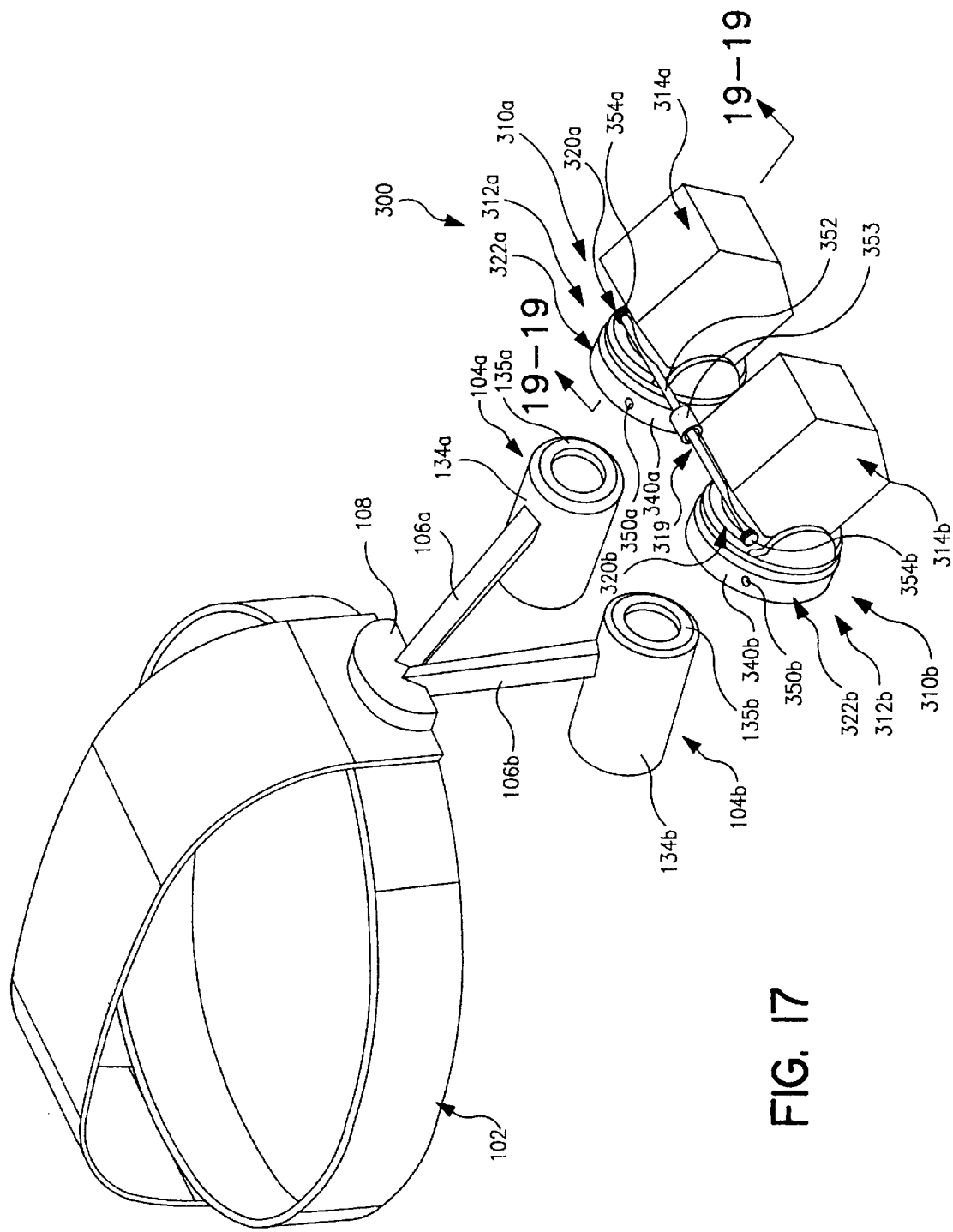
FIG. 17 is a perspective view of a third embodiment of the present invention detached from an adjustable head mounted loupes system.

Referring to FIGS. 17–20 a third embodiment, top aligned ball and socket (TABS) embodiment 300, of the present invention, is shown. It should be noted that TABS 300 although shown in FIG. 17 with adjustable head mounted system 102, could be attached to any of the aforementioned types of surgical loupes. Referring to FIG. 17, TABS 300 includes a housing having a left and right ball member 320a, 320b; an attachment member having a left and right socket member 322a, 322b to secure housing members 320a, 320b to loupes barrel 104a, 104b; an optical member including two Penta prisms 314a, 314b one for each housing member 320a, 320b; an alignment member 319 to maintain the orientation of prisms 314a, 314b relative to barrels 104a, 104b; a coupling member 317 to secure prisms 314a, 314b to housing members 320a, 320b. Both the left and right loupes barrels 104a, 104b of adjustable head mounted surgical loupes 102 are identical. The left and right attachment members 322a, 322b and left and right housing members 320a, 320b are also identical. For convenience, the structure and function of right attachment member 322a, right housing member 320a and right loupes barrel 104a will be discussed with the understanding that the structure and function of the left attachment member 312b, left housing member 320b and left loupes barrel 104b are identical.

Figure 18:
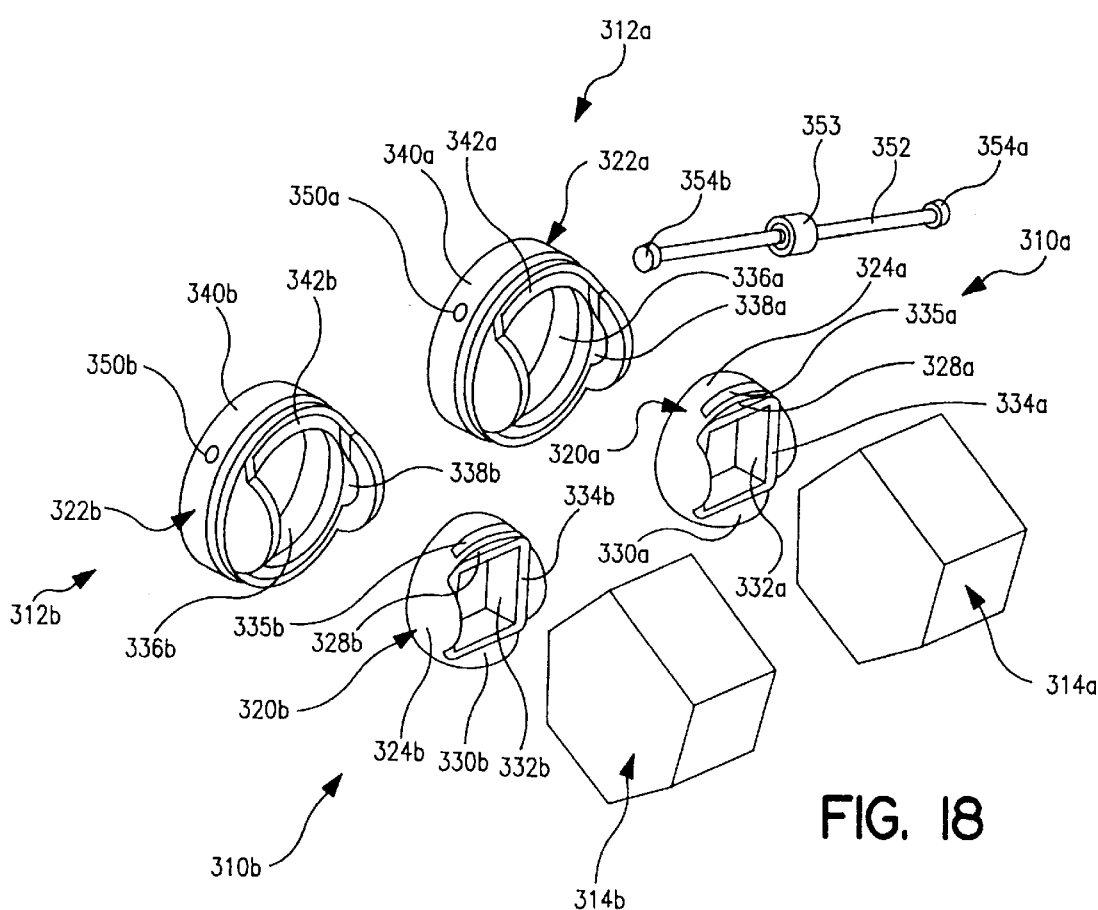
FIG. 18 is an exploded, perspective view of the third embodiment shown in FIG. 17.
Figure 19:
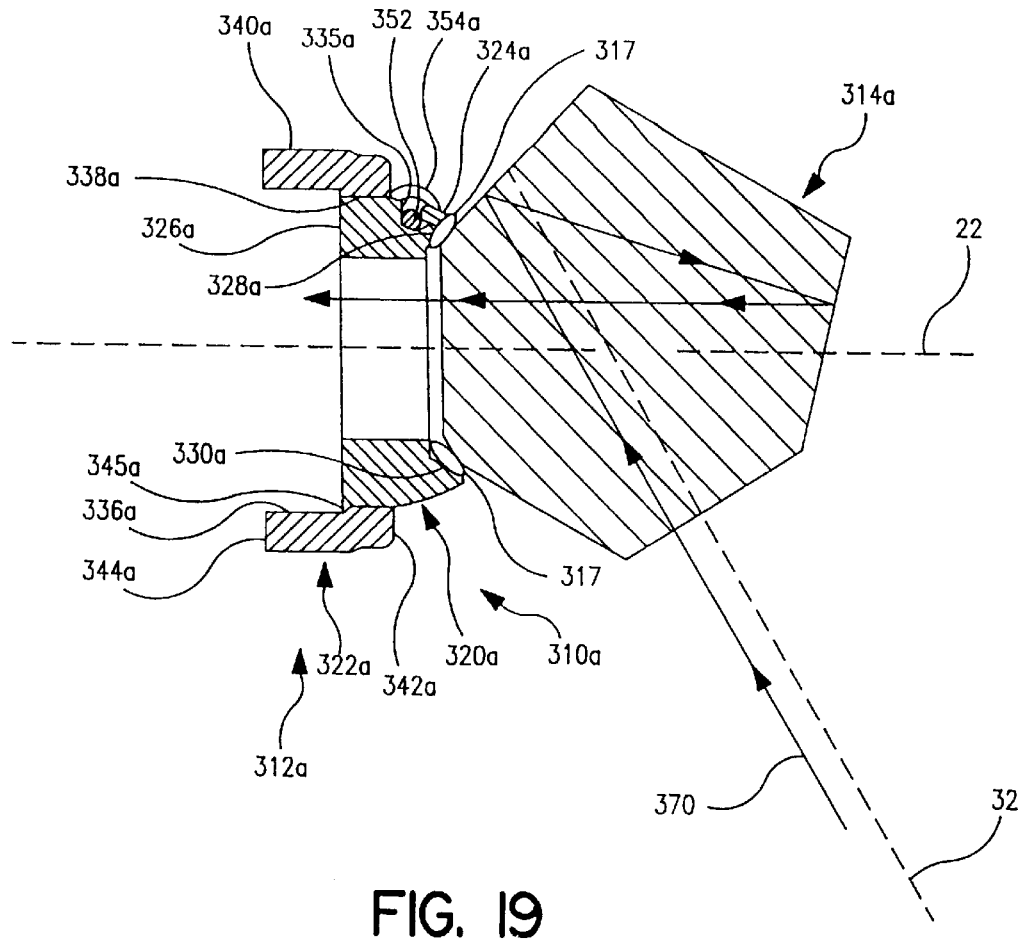
FIG. 19 is a cross sectional view of the embodiment shown in FIG. 17 taken along lines 19—19 shown in FIG. 17.

As shown in FIGS. 18 and 19, housing ball member 320a has a partial, spherical, outward-facing surface 324a; an axial, outward-facing, planer surface 326a; an upper, optical member attachment surface 328a; a lower, optical member attachment surface 330a; a radial, inward-facing clearance surface 332a and an axial, outward facing surface 334a. Spherical surface 324a has a key slot 335a formed therein.

Referring to FIGS. 18 and 19, socket member 322a has a radial, inward-facing sleeve surface 336a; an inward-facing, partial, spherical surface 338a; a radial, outward-facing surface 340a; an axial, outward-facing surface 342a; an axial, outward-facing end surface 344a and an axial, outward-facing surface 345a. Socket member 322a has an interior, axial cavity defined by socket sleeve surface 336a and socket spherical surface 338a.

Ball member 320a is disposed within the axial cavity of socket member 322a such that socket spherical surface 338a and ball spherical surface 324a are in contact, ball axial, inward facing, planer surface 326a is flush with socket axial, outward-facing surface 345a and key slot 335a is disposed outward from socket outward-facing axial surface 342a. Socket sleeve surface 336a is then slide over the radial, outward-facing loupes barrel surface 134a. The axial, outward-facing loupes barrel surface 135a contacts ball axial, outward-facing, planer surface 326a, thereby biasing ball member 320a forward into the cavity of socket member 322a. Therefore, socket member 322a captively holds ball member 320a against loupes axial surface 135a.

Socket member 322a has a set screw aperture 350a (shown in FIG. 17) that extends normal to and between socket sleeve surface 336a and socket radial outward-facing surface 340a. A set screw, not shown, is threaded into set screw aperture 350a to fixably attach socket member 322a to the loupes barrel 104a. Those skilled in the art will know that alternative common methods could be used to secure socket member 322a to loupes barrel 104a, such as an adhesive or mating threaded surfaces. Once assembled, ball member 320a is free to rotate relative to socket member 322a about their common spherical center defined by socket spherical surface 338a and ball spherical surface 324a.

Figure 20:
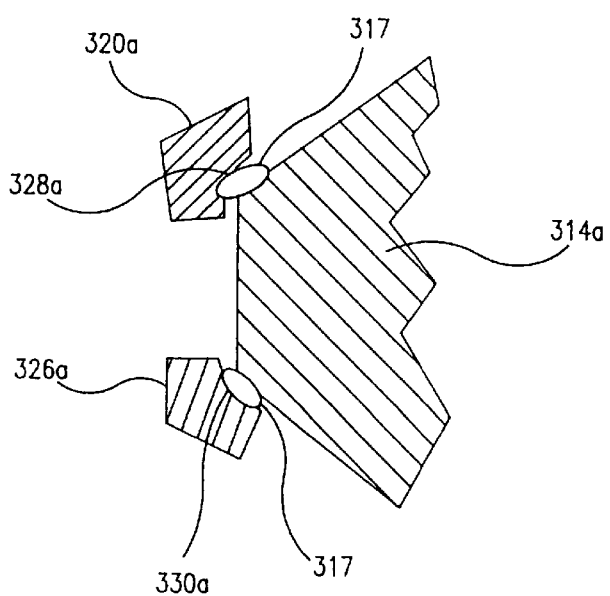
FIG. 20 is a cross sectional view of a portion of the embodiment shown in FIG. 19.

Prisms 314a, 314b are attached to upper optical alignment surfaces 328a, 328b and lower optical alignment surfaces 330a, 330b by coupling member 317 (shown in detail in FIG. 20). Coupling member 317 is an adhesive such as epoxy. Coupling member 317 could be an standard technique used to mount optical elements to a surface. For example, a felt pad could be used in conjunction with an adhesive. It is also within the scope of the present invention, for coupling member 317 to be a solid member to fix prisms 314a, 314b. An example would be a snap feature molded into housing members 320a, 320b to fixedly hold the edges of prisms 314a, 314b. Light enters TABS 300 from desired direction 32 and is redirected into the optic assemblies 18 of loupes barrel 104a, 104b along the loupes optical axis 22 as shown pictorially by ray 370 in FIG. 19.

Key slot 335a in ball member 320a provides a partial cylindrical groove for alignment member 319 to engage. Alignment member 319 (shown in FIGS. 17 and 18) consists of a circular rod 352, whose diameter is generally identical to the diameter of cylindrical key slot 335a, with circular end caps 354a, 354b of a relatively larger diameter than alignment rod 352 and a grip 353 centered along rod 352. Alignment rod 352 snaps into key slot 335a, 335b on both the left and right ball members 320a, 320b. Alignment member 319 orients key slot 335a in left ball member 320a parallel to key slot 335b in right ball member 320b. This orientation also makes upper optical alignment surfaces 328a, 328b and lower optical alignment surfaces 330a, 330b parallel to each other, more specifically co-planer. This parallelism is important to maintaining image quality and clarity. A deviation from parallel, more specifically co-planer, will result in a misalignment between the images formed by the left and right eyes of the user.

Alignment member 319 maintains this parallel, more specifically co-planer, orientation when loupes barrels 104a, 104b are moved. As discussed earlier, when loupes barrels 104a, 104b are moved outward, relative to each other, they also move upward. Conversely, when they are moved inward, relative to each other, they move downward. Alignment member 319 causes ball member 320a, 320b to rotate when loupes barrels 104a, 104b are moved. This rotation is due to alignment rod 352 being held captive by key slots 335a, 335b. The rod is free to slide along its axial extent within key slot 335a, 335b, but is held captive in its radial extent. It will be appreciated by those skilled in the art that alignment member 317 could be a flat bar coupled to prisms 314a, 314b. In this scenario, key slots 335a, 335b can be deleted. The main requirement for alignment member 319 is that it is rigid enough to force the rotation of ball members 320a, 320b relative to socket members 322a, 322b.

Figure 21:
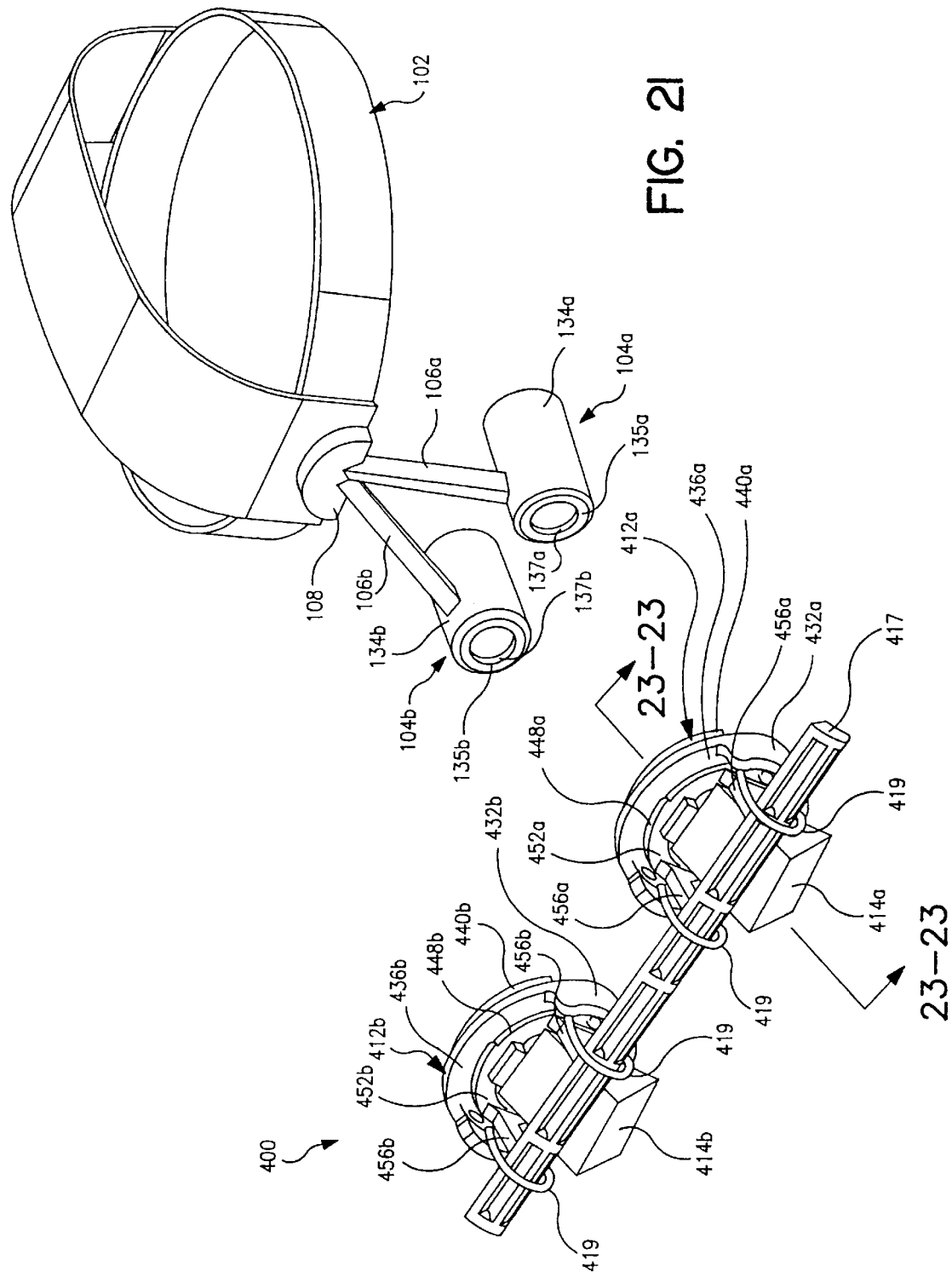
FIG. 21 is a perspective view of a fourth embodiment of the present invention detached from an adjustable head mounted loupes system.
Figure 22:
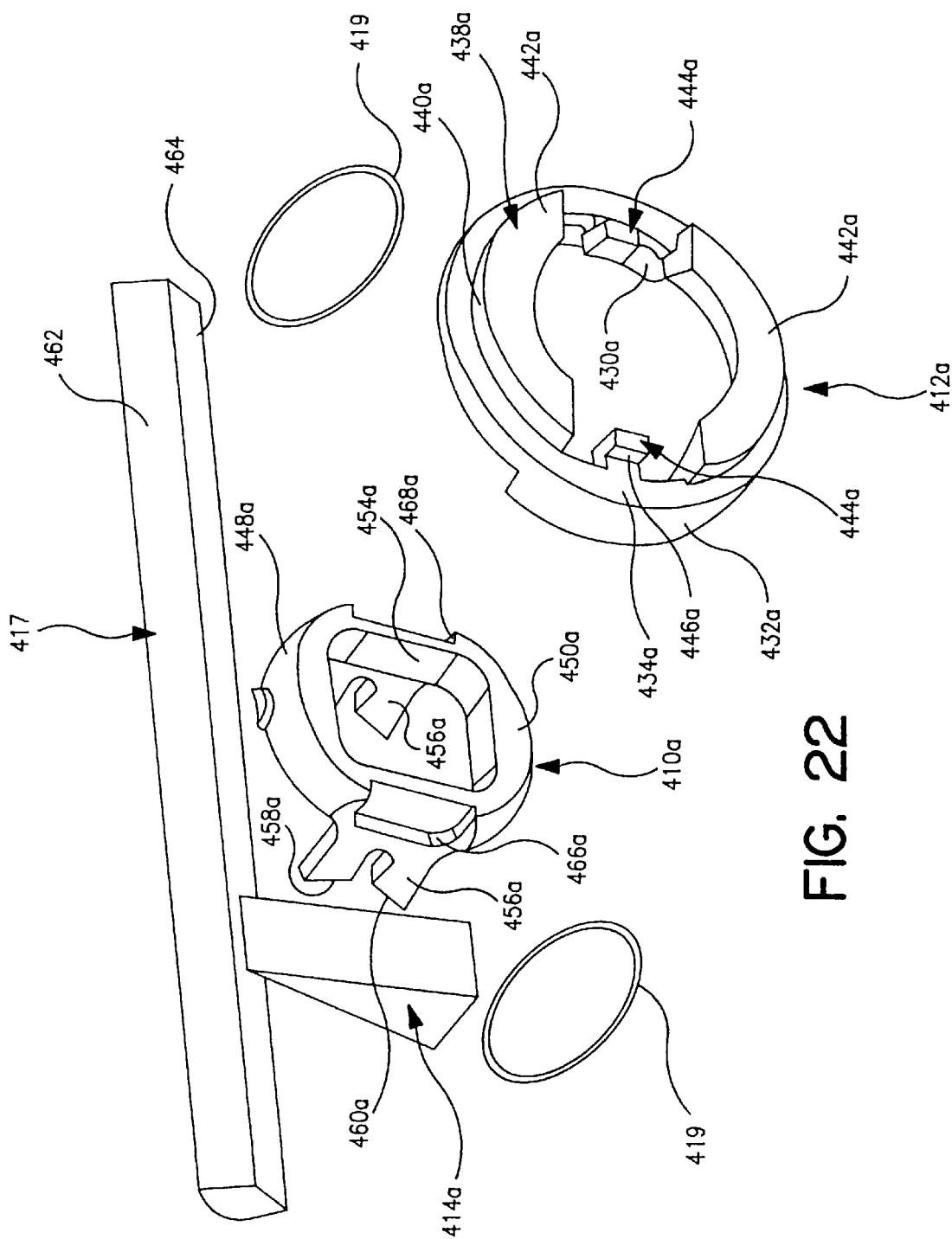
FIG. 22 is an exploded, perspective view of the embodiment shown in FIG. 21.
Figure 23:
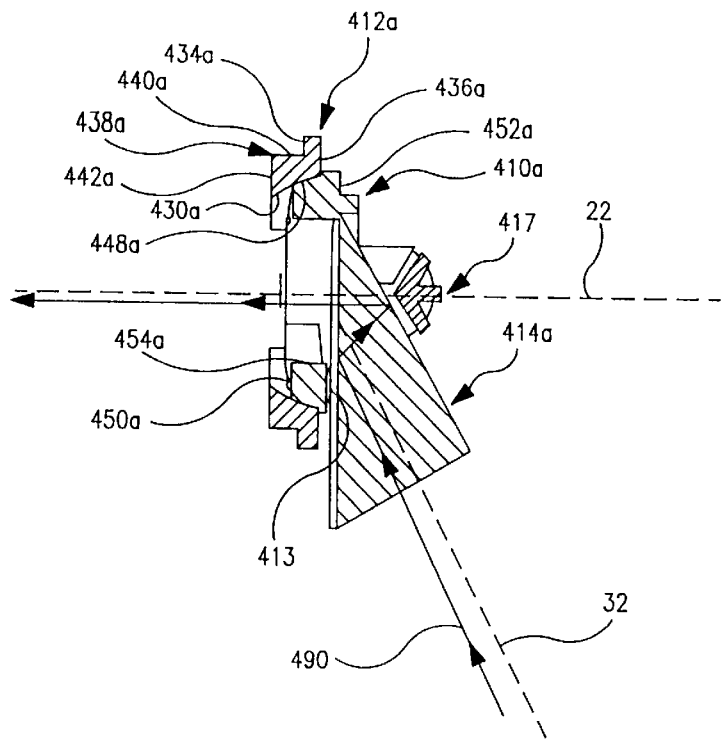
FIG. 23 is a cross sectional view of the embodiment shown in FIG. 21 taken along lines 23—23 shown in FIG. 21.

FIGS. 21–23 show a fourth embodiment of the present invention, a front aligned ball and socket (FABS) 400, is shown. FABS 400 is discussed in operation with adjustable head mounted surgical loupes 102 presented earlier in this disclosure.

Referring to FIGS. 21 and 22, FABS 400 includes a housing having a left and right ball member 410a, 410b; an attachment member including a pair of socket members 412a, 412b; an optical member including a pair of Littrow prisms 414a, 414b; an alignment member including a bar 417 and elastic straps 419; and a coupling member 413 (shown in FIG. 23). The left and right housing members 410a, 410b are identical. The left and right attachment members 412a, 412b and prisms 414a, 414b are identical. For convenience, therefore, the structure and function of the right housing member 410a, right attachment member 412a and right prism 414a will be discussed with the understanding that the structure and function of the left housing member 410b, left attachment member 412b and left prism 414b are identical.

As shown in FIG. 22, attachment member 412a has a radial inward-facing, partial, spherical surface 430a; a radial outward-facing perimetral surface 432a; an axial outward-facing surface 434 and an axial outward-facing surface 436a. Attachment member 412a has two protrusions 438a extended outward from 438a have a radial, outward-facing Protrusions 438a have a radial, outward-facing collar surface 440a and an axial, outward-facing surface 442a. Attachment collar surface 440a is press fit into loupes radial inward-facing surface 137a such that attachment axial, outward-facing surface 442a is oriented toward the loupes barrel and attachment axial outward-facing surface 434a comes to rest on loupes axial outward-facing surface 135a. It should be noted that attachment collar surface 440a could be adhesively attached to loupes barrel 104a, threaded into loupes barrel 104a or attached by any commonly known manner.

Attachment member 412a contains an axial, interior clearance cavity that extends from axial surface 436a completely through to attachment outward-facing axial surface 442a and whose extent is defined by attachment spherical surface 430a. This cavity allows light to pass through attachment member 412a into the optical assemblies of the loupes barrel 104a.

There are two attachment hook members 444a (shown in FIG. 22) extending radially inward from attachment spherical surface 430a at axial outward-facing surface 434a and then extending axially, outward toward axial outward-facing surface 442a. Hook members 444a are used to secure the housing member 410a and alignment bar 417 to attachment member 412a. Each hook 444a has a catch surface 446a to capture a portion of alignment strap 419. Straps 419 can be any elastic band, wire or equivalent item.

As shown in FIG. 22, housing member 410a has a spherical, outward-facing surface 448a; an axial outward-facing surface 450a; an outward-facing, optical mounting surface 452a; and an axial, interior, clearance cavity defined by radial, inward-facing surfaces 454a. The clearance cavity allows light from desired direction 32 to travel through FABS 400 into loupes barrel 104a. Housing member 410a is disposed such that outward-facing, spherical surface 448a is in contact with attachment inward-facing, spherical surface 430a.

Housing member 410a has alignment member support members 456a which extend axially outward from housing optical mounting surface 452a. Support members 456a have a centering channel defined by channel surfaces 458a and 460a. Channel surfaces 458a, 460a mate against matched centering surfaces 462 and 464 on alignment bar member 417.

Housing member 410a has two additional axial, interior cavities defined by surface sets 466a and 468c. These cavities are outboard of the clearance cavity and are located next to support members 456a. These cavities allow alignment strap 419, secured to attachment hook members 444c, to pass through housing member 410a and engage alignment bar member 417.

Prism 414a is adhesively attached to housing optical mounting surface 452a by coupling member 413 (shown in FIG. 23). In all embodiments, it should be noted that common optical mounting techniques should be used. One example is using a felt pad in conjunction with epoxy to adhere prism 414a to housing optical mounting surface 452a. A Littrow prism is shown in FIGS. 21–23 as FABS optical member 414a. As in previous embodiments, the optical member is not limited to only being a Littrow prism. However, if a different optical member was used, then the shape of housing optical mounting surface 452a might need to be changed to reflect the new geometry.

FABS 400 is assembled in the following manner. First, attachment member 412a is secured to the loupes barrel 104a by methods previously discussed. Second, prism 414a is coupled to housing member 410a by coupling member 413. Third, housing member 410a is aligned to attachment member 412a such that housing spherical surface 448a is in contact with attachment spherical surface 430a and such that housing interior cavities defined by surface sets 466a, 468a line up with attachment hook members 444a. Fourth, alignment straps 419 are positioned around attachment hook members 444a such that straps 419 are captured by alignment hook catch surface 446a and such that straps 419 extend through the interior cavities of housing member 410a defined by surface sets 466a, 468a. Finally, alignment bar member 417 is inserted into the interior of straps 419 and positioned such that centering surfaces 462, 464 rest against housing channel surfaces 458a, 460a. The length and elasticity of straps 419 should be such that they hold alignment bar member 417 and housing member 410a flush against attachment member 412a.

Housing member 410a, once assembled, is free to rotate relative to attachment member 412a. Alignment bar 417 maintains housing members 410a, 410b and prisms 414a, 414b in the correct orientation with respect to loupes barrels 104a, 104b. Prisms 414a, 414b should remain parallel, more specifically co-planer, to each other to insure that the optical axes 22 of loupes barrels 104a, 104b still converge.

As discussed earlier, when loupes barrels 104a, 104b are moved outward, relative to each other, they also move upward. Conversely, when they are moved inward, relative to each other, they move downward. Alignment bar 417 causes housing members 410a, 410b to rotate when loupes barrels 104a, 104b are moved. This rotation is due to alignment bar 417 being held against support members 456a, 456b by straps 419. Prisms 414a, 414b are secured to and rotate with housing members 410a, 410b. Therefore, by causing housing members 410a, 410b to rotate, alignment bar 417 and straps 419 maintain the orientation of prisms 414a, 414b relative to loupes 104a, 104b.

A ray 490, shown in FIG. 23, gives a pictorial view of how light from desired direction 32 travels through FABS 400 and into loupes barrel 104a along loupes optic axis 22.

All of the aforementioned embodiments can be used with a static surgical loupes system like a through-the-eyeglass system. Since the loupes barrels in such a system do not move, the alignment member of the present invention serves the primary function of calibrating the orientation of the optical member relative to the loupes barrels.

Figure 24:
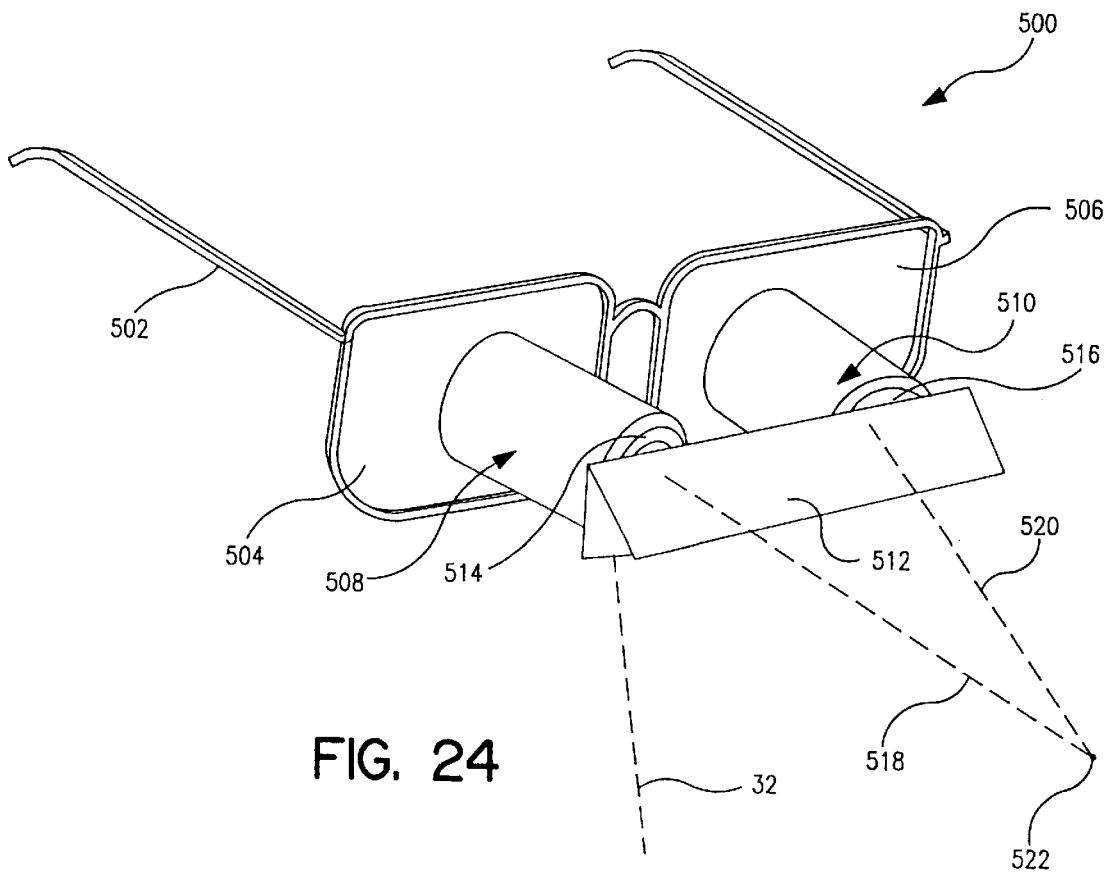
FIG. 24 is a perspective view of a surgical loupes system.

FIG. 24 shows a surgical loupes 500 including: an eyeglass frame 502 having a two lenses 504, 506; two barrels 508, 510 each including an optical assembly with an optical axis 518, 520; and a optical redirection member 512 to redirect light from a desired direction 32 into the optical assemblies of barrels 508, 510.

Barrels 508, 510 are secured to lenses 504, 506 respectively. Apertures are formed in lenses 504, 506 to receive barrels 508, 510. Barrels 508, 510 can be secured either with a press fit or with an adhesive. Barrels 508, 510 are oriented such that their respective optical axes 518, 520 converge to a point in space 522. The optical axis 518, 520 shown in FIG. 24 are only for the optical assemblies of barrels 508, 510. The optical axis 518, 520 do not show the effect of having optical redirection member 512 positioned in front of barrels 508, 510. Because of optical redirection member 512 light will enter barrels 508, 510 from another point in space along the desired direction 32 instead of from point 522.

Barrels 508, 510 each have a front surface 514 and 516. Surfaces 514 and 516 are co-planar and serve as a mounting surface for optical redirection member 512. Optical redirection member 512 is shown as one prism in FIG. 24. However, optical redirection member 512 can be two separate prisms, one attached to each surface 514, 516. Optical redirection member 512 can also be at least one mirror positioned in at least one housing, at least one prism positioned in at Icast one housing, or at least one optical assembly positioned in at least one housing.

If optical redirection member 512 is composed of two separate members, one for each barrel, the members will need to be aligned during manufacture such that optical assemblies 518, 520 of barrels 508, 510 still converge to a point in space. Optical redirection member 512 can be secured to barrels 508, 510 with an adhesive or any other commonly used optical mounting technique. It is within the scope of the present invention to make the optical redirection member 512 an integral part of barrels 508, 510.

Although the invention has been described in detail with reference to certain preferred embodiments, variations and modifications exist within the scope and spirit of the present invention as described and defined in the following claims.

We claim:

1. An apparatus for changing the direction of light incident on a surgical loupes, the loupes having two optical barrels moveable relative to each other and each optical barrel having an optical assembly with an optical axis, comprising:

a housing;

at least one optical member for redirecting light incident onto said optical assemblies from a desired direction at an angle to the optical axis of said optical assemblies;

a member for coupling the at least one optical member to the housing;

an attachment member to secure said housing to the barrels; and an alignment member for orienting the at least one optical member to redirect the light from said desired direction generally along the optical axes of said optical assemblies of the barrels and for maintaining the orientation of the at least one optical member relative to the optical assemblies of the barrels when the barrels are moved.

2. The apparatus as recited in claim 1, wherein:

said alignment member calibrates the orientation of the at least one optical member relative to the optical assemblies of the barrels.

3. The apparatus as recited in claim 1, wherein:

said alignment member includes a partially exposed, linear cavity; and a portion of said attachment member is disposed within said linear cavity of said alignment member such that when said optical barrels are moved said attachment member is constrained to move along said linear cavity.

4. The apparatus as recited in claim 3, wherein:

said portion of said attachment member includes a partial, spherical surface; and said linear cavity of said alignment member includes a cylindrical surface the radius of which is generally matched to the radius of said attachment member spherical surfaces.

5. The apparatus as recited in claim 1, wherein:

said alignment member includes a partially exposed, linear cavity;

said attachment member includes a partial, spherical surface; and wherein said spherical surface of said attachment member is disposed within said linear cavity of said alignment member such that when said optical barrels are moved said attachment member is constrained to move only said linear cavity.

6. The apparatus as recited in claim 1, wherein:

said attachment member includes a left and right attachment member each having a partial, spherical surface;

said housing member includes a left and right member each having a partial, spherical surface;

said left and right attachment members position said housing left and right members such that said left and right housing members are adjacent to said loupes and said left and right housing member spherical surfaces are adjacent to said left and right attachment member spherical surfaces;

said left housing member is rotatable relative to said left attachment member; and said right housing member is rotatable relative to said right attachment member.

7. The apparatus as recited in claim 6, wherein:

said left and right housing members each have a partially exposed, linear groove formed therein; and said alignment member includes a linear member which is coupled to said linear groove in both said left and right housing members such that said left and right housing members maintain their orientation relative to each other as said left and right housing members rotate due to movement of said loupes barrels.

8. The apparatus as recited in claim 6, further comprising:

a second coupling member to secure said alignment member to said at least one optical member; and wherein, said at least one optical member is comprised of a left and right optical member with said right optical member coupled to said right housing member and said left optical member coupled to said left housing member.

9. The apparatus as recited in claim 1, wherein:

said alignment member includes a linear member;

said attachment member includes a left and right attachment member each having a partial, spherical surface;

said housing member includes a left and right member each having a partial, spherical surface;

said left and right attachment members position said housing left and right members such that said left and right housing members are adjacent to said loupes and said left and right housing member spherical surfaces are adjacent to said left and right attachment member spherical surfaces;

said left housing member is rotatable relative to said left attachment member; and said right housing member is rotatable relative to said right attachment member.

10. The apparatus as recited in claim 9, wherein:

said left and right housing members each have a partially exposed, linear groove formed therein; and said alignment linear member is coupled to said linear groove in both said left and right housing member spherical surfaces such that said left and right housing members maintain their orientation relative to each other as said left and right housing members rotate due to movement of said loupes barrels.

11. The apparatus as recited in claim 1, wherein:

said attachment member includes a left and right attachment member each having a partial, spherical surface;

said housing member includes a left and right member each having a partial, spherical surface;

said left and right housing member spherical surfaces are generally positioned next to said left and right attachment member spherical surfaces respectively;

said left housing member is rotatable relative to said left attachment member; and said right housing member is rotatable relative to said right attachment member.

12. The apparatus as recited in claim 11, wherein:

said left and right housing members each have at least one support member; and said left and right attachment members each have at least one retaining member;

said alignment member includes a linear member and at least one strap members;

said alignment linear member rests on the at least one support members of said left and right housing members; and said at least one alignment strap members couple said alignment linear member to each of said left and right attachment members at their at least one retaining members.

13. The apparatus as recited in claim 1, wherein:

said housing includes a moveable portion which moves relative to the remaining portion of said housing;

said coupling member is positioned between said moveable portion and said at least one optical member such that when said moveable portion is moved said at least one optical member moves as well.

14. An apparatus for changing the direction of light incident on a surgical loupes, the loupes having two optical barrels moveable relative to each other and each optical barrel having an optical assembly with an optical axis, comprising:

a housing;

at least one optical member for redirecting light incident onto said optical assemblies from a desired direction at an angle to the optical axis of said optical assemblies;

a member for coupling the at least one optical member to the housing;

an attachment member to secure said housing to the barrels; and an alignment member for calibrating the orientation of the at least one optical member relative to the optical assemblies of the barrels so that the at least one optical member is oriented to redirect the light from said desired direction generally along the optical axes of said optical assemblies of the barrels.

15. An apparatus for changing the direction of light incident on a surgical loupes, the loupes having two optical barrels each optical barrel having an optical assembly with an optical axis, comprising:

a housing;

at least one optical member for redirecting light incident onto said optical assemblies from a desired direction at an angle to the optical axis of said optical assemblies;

a member for coupling the at least one optical member to the housing;

an attachment member to secure said housing to the barrels; and an alignment member for calibrating the orientation of the at least one optical member relative to the optical assemblies of the barrels so that the at least one optical member is oriented to redirect the light from said desired direction generally along the optical axes of said optical assemblies of the barrels.

16. An apparatus for changing the direction of light incident on a surgical loupes, the loupes having two optical barrels moveable relative to each other and each optical barrel having an optical assembly with an optical axis, comprising:

at least one optical member for redirecting light incident onto said optical assemblies from a desired direction at an angle to the optical axis of said optical assemblies;

an attachment member to secure said at least one optical member to the barrels; and an alignment member for orienting the at least one optical member to redirect the light from said desired direction generally along the optical axes of said optical assemblies of the barrels and for maintaining the orientation of the at least one optical member relative to the optical assemblies of the barrels when the barrels are moved.

17. An apparatus for changing the direction of light incident on a surgical loupes, the loupes having two optical barrels each optical barrel having an optical assembly with an optical axis, comprising:

at least one optical member for redirecting light incident onto said optical assemblies from a desired direction at an angle to the optical axis of said optical assemblies;

an attachment member to secure said at least one optical member to the barrels; and an alignment member for calibrating the orientation of the at least one optical member relative to the optical assemblies of the barrels so that the at least one optical member is oriented to redirect the light from said desired direction generally along the optical axes of said optical assemblies of the barrels.

18. A surgical loupes comprising:

a pair of eyeglass frames;

a left barrel member coupled to said eyeglass frames and containing an optical assembly with an optical axis and having a front exterior barrel surface;

a right barrel member coupled to said eyeglass frames and containing an optical assembly with an optical axis and having a front exterior barrel surface, wherein said right barrel front surface is co-planar with said left barrel front surface;

wherein said optical axes of said left and right barrel members converge at a point in space; and at least one optical member secured to said left barrel front surface and said right barrel front surface for redirecting light incident onto said optical assemblies from a desired direction at an angle to the optical axis of said optical assemblies, wherein when the at least one optical member is secured to the left barrel front surface and the right barrel front surface light from the desired direction is directed through the optical assemblies and when the at least one optical member is not secured to the left barrel front surface and the right barrel front surface light from a second direction is directed through the optical assemblies.

19. The surgical loupes as recited in claim 18, wherein said at least one optical member is a continuous member spanning both said left barrel member and said right barrel member.

20. The surgical loupes as recited in claim 18, wherein said at least one optical member is comprised of a left optical member and a right optical member; said left optical member coupled to said front surface of said left barrel member; and said right optical member coupled to said front surface of said right barrel member.

* * * * *